(12) United States Patent
Zhao et al.

(10) Patent No.: US 12,319,844 B2
(45) Date of Patent: Jun. 3, 2025

(54) BODY FLUID RESISTANT TISSUE ADHESIVES

(71) Applicants: Massachusetts Institute of Technology, Cambridge, MA (US); Mayo Foundation for Medical Education and Research, Rochester, MN (US)

(72) Inventors: Xuanhe Zhao, Allston, MA (US); Hyunwoo Yuk, Cambridge, MA (US); Xinyu Mao, Cambridge, MA (US); Christoph Nabzdyk, Rochester, MN (US)

(73) Assignees: MASSACHUSETTS INSTITUTE OF TECHNOLOGY, Cambridge, MA (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 18/535,124

(22) Filed: Dec. 11, 2023

(65) Prior Publication Data
US 2024/0132758 A1    Apr. 25, 2024

Related U.S. Application Data

(62) Division of application No. 17/110,841, filed on Dec. 3, 2020, now Pat. No. 11,884,845.

(60) Provisional application No. 62/942,874, filed on Dec. 3, 2019.

(51) Int. Cl.
*C09J 105/08* (2006.01)
*A61L 24/00* (2006.01)
*C09J 9/00* (2006.01)
*C09J 11/06* (2006.01)
*C09J 133/02* (2006.01)
*C09J 151/00* (2006.01)

(52) U.S. Cl.
CPC ......... *C09J 105/08* (2013.01); *A61L 24/0042* (2013.01); *A61L 24/0094* (2013.01); *C09J 9/00* (2013.01); *C09J 11/06* (2013.01); *C09J 133/02* (2013.01); *C09J 151/003* (2013.01); *A61L 2400/04* (2013.01); *C09J 2483/00* (2013.01)

(58) Field of Classification Search
CPC ........ C09J 105/08; C09J 133/02; C09J 11/06; C09J 9/00; C09J 151/003; C09J 2483/00; A61L 24/0094; A61L 24/0042; A61L 2400/04

See application file for complete search history.

(56) References Cited

FOREIGN PATENT DOCUMENTS

WO    WO 2007/099370    *   9/2007    ........... A61L 15/225

* cited by examiner

*Primary Examiner* — Shirley V Gembeh
(74) *Attorney, Agent, or Firm* — Nieves IP Law Group, LLC; Peter A. Nieves

(57) ABSTRACT

A tissue adhesive material that provides fast and robust adhesion even on tissue surfaces covered in bodily fluids. The tissue adhesive material is formed of a hydrophobic matrix and a plurality of bioadhesive microparticles dispersed within the hydrophobic matrix configured such that disposing the adhesive material directly on a fluid covered surface and applying pressure causes the (a) hydrophobic matrix to repel the fluid, (b) the bioadhesive particles to compress forming an adhesive layer, and (c) the bioadhesive particles to form temporary crosslinks followed by covalent crosslinks with the surface.

20 Claims, 28 Drawing Sheets

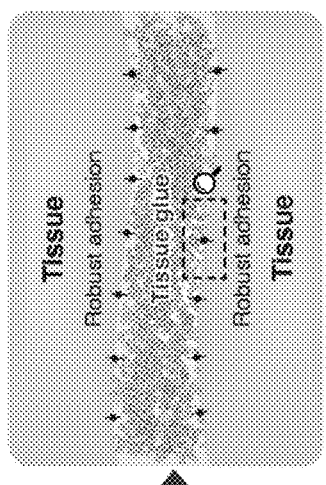
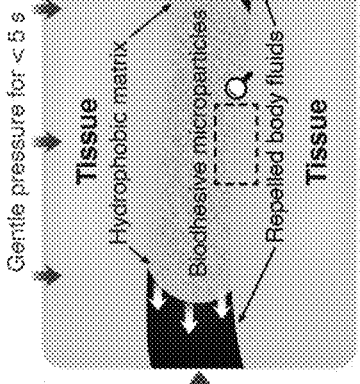
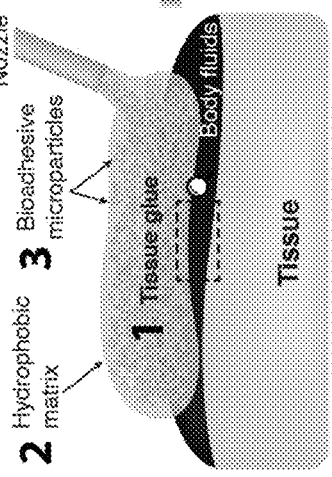

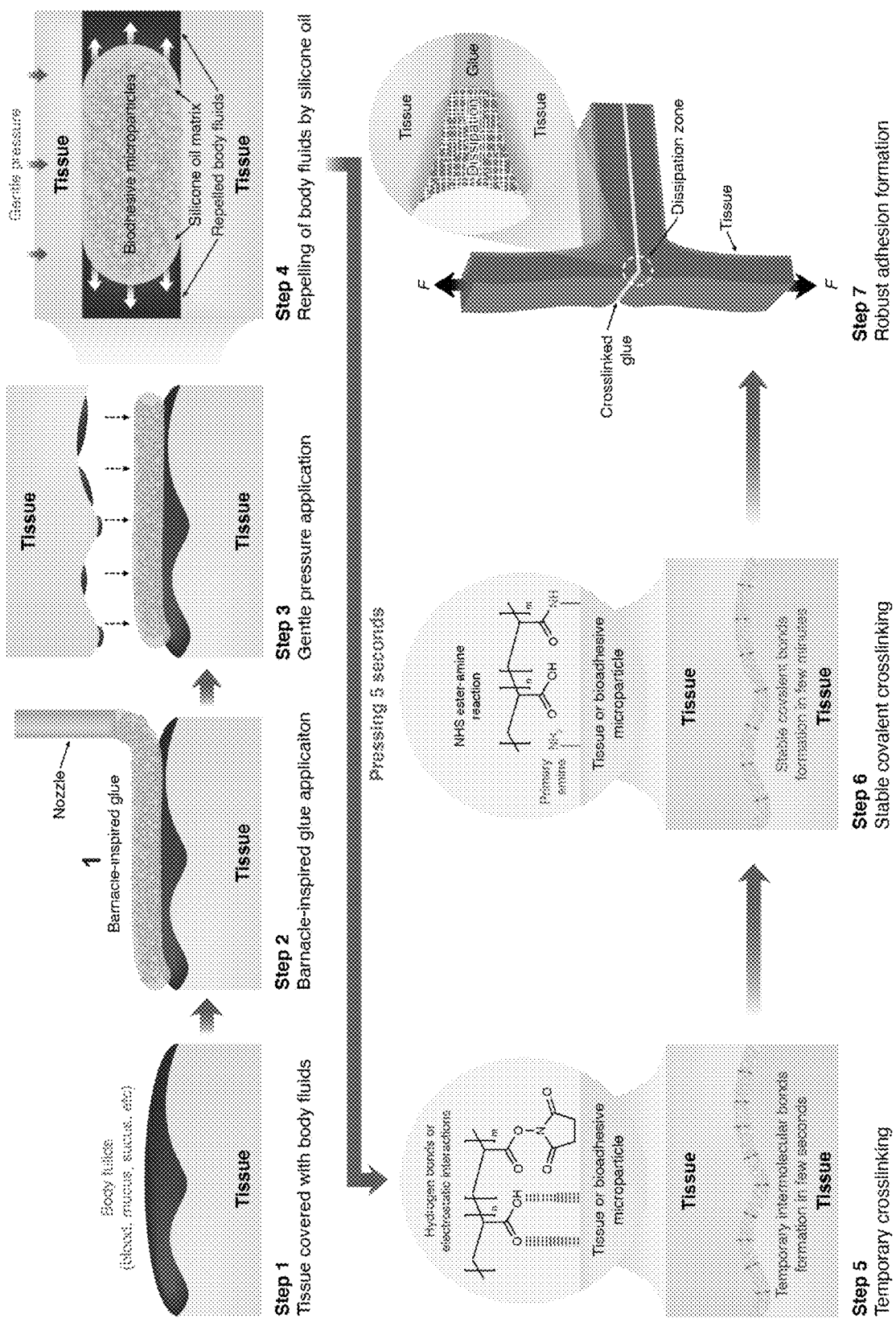

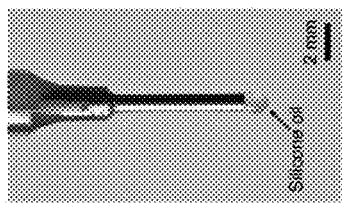
FIG. 8A
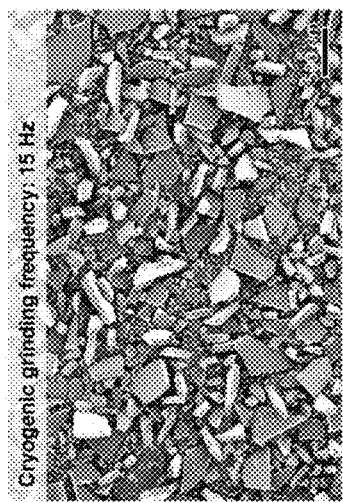
FIG. 8B
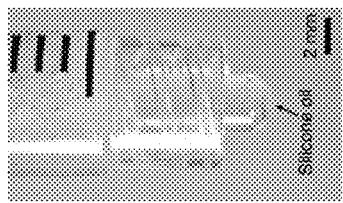
FIG. 8C
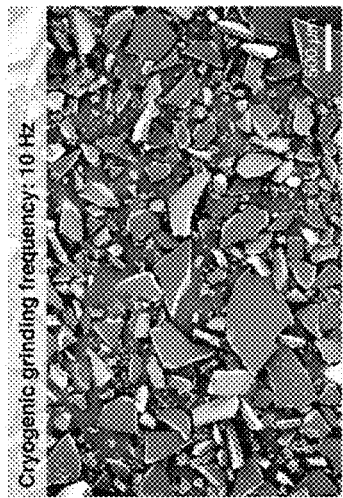
FIG. 8D
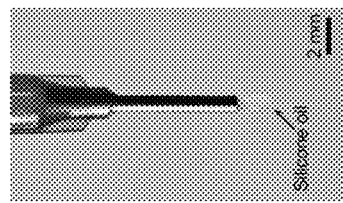
FIG. 8E
FIG. 8F
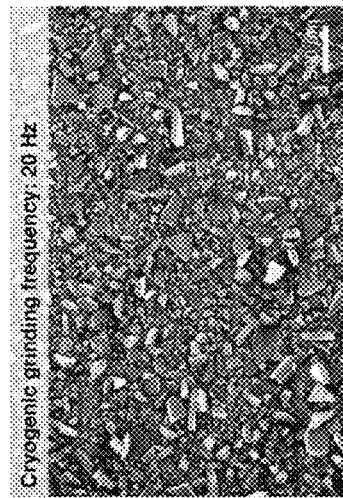
FIG. 8G
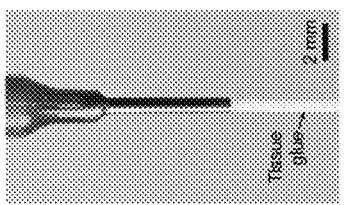
FIG. 8H
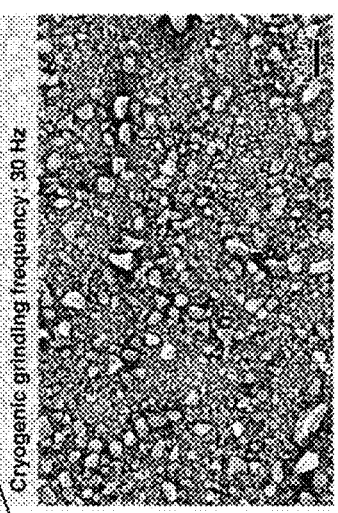
FIG. 8I
FIG. 8J FIG. 10A
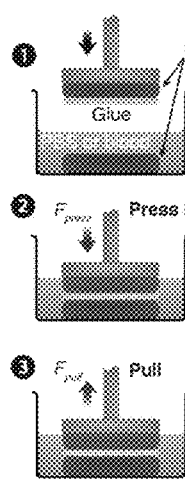
FIG. 10B
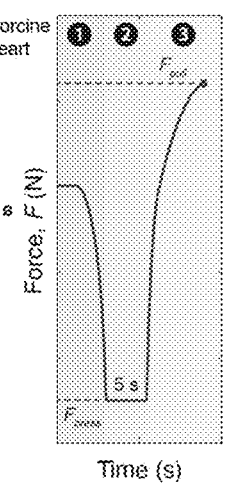
FIG. 10C
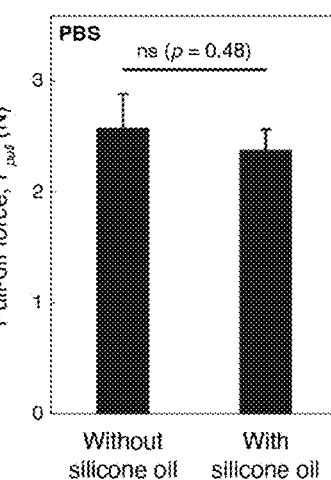
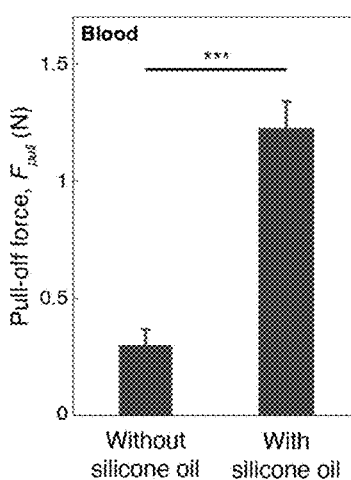
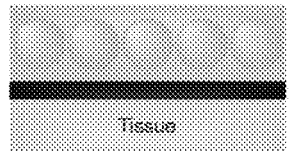
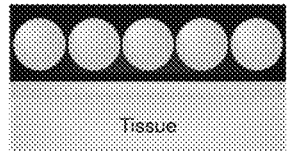
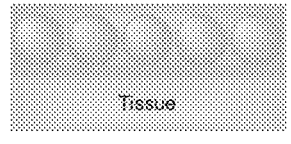
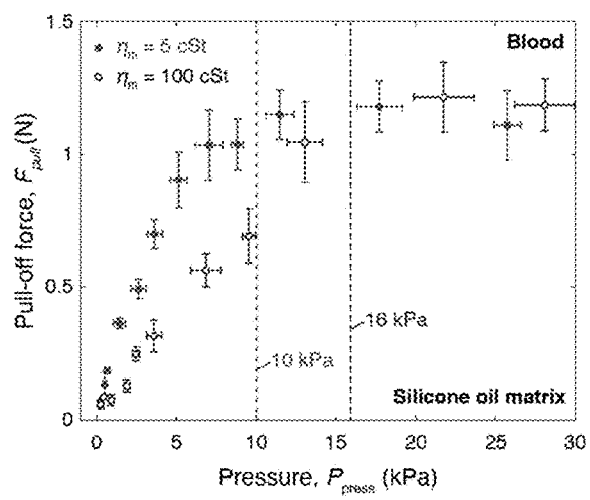
FIG. 10D
FIG. 10E FIG. 13A 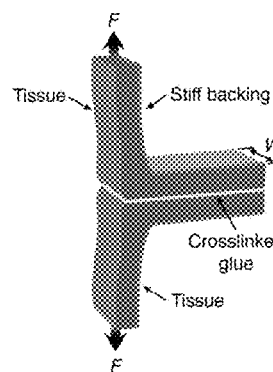 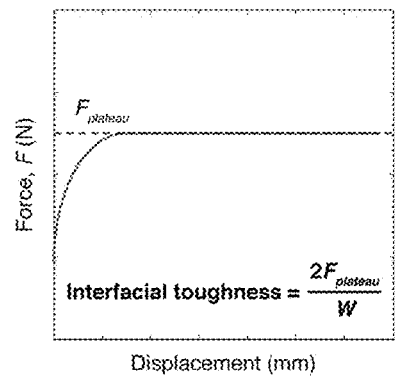 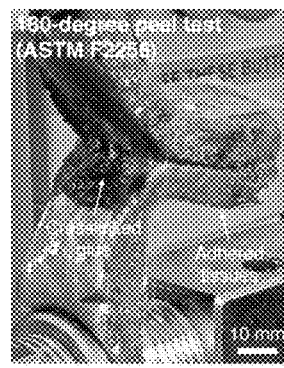
FIG. 13B 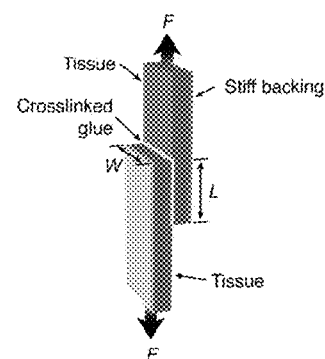 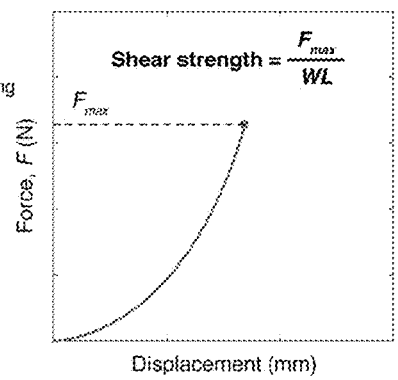 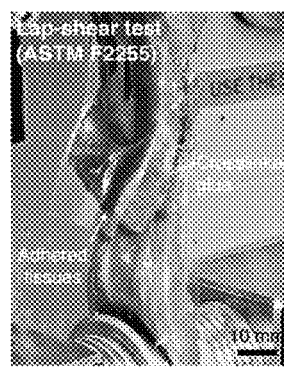
FIG. 13C 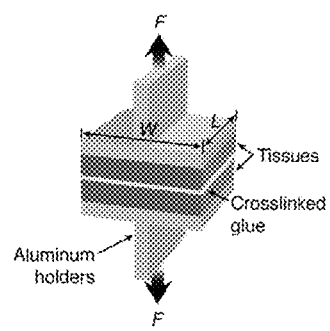 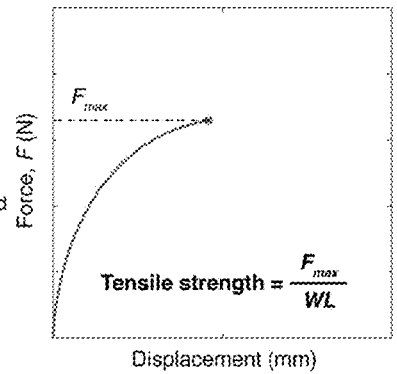 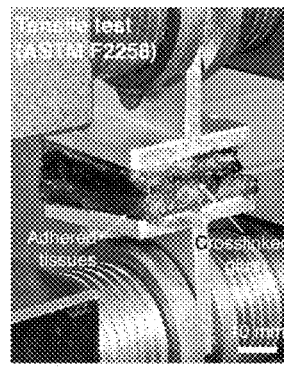

FIG. 14A
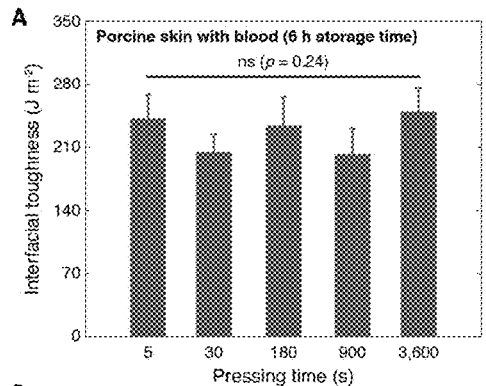
FIG. 14B
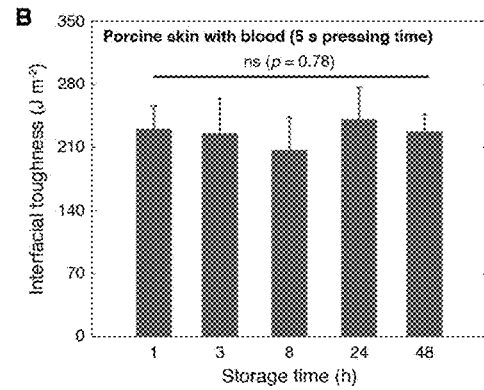
FIG. 14C
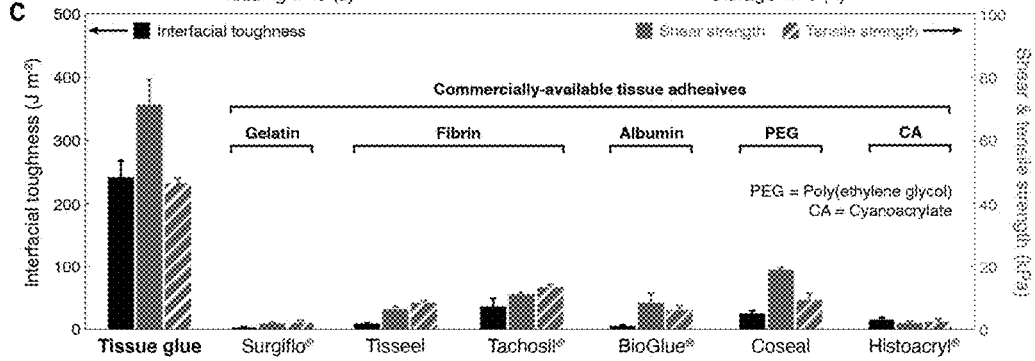
FIG. 14D
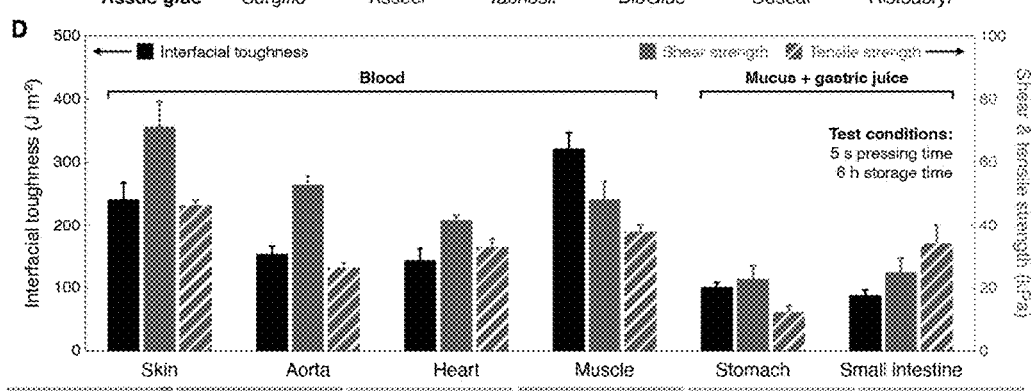
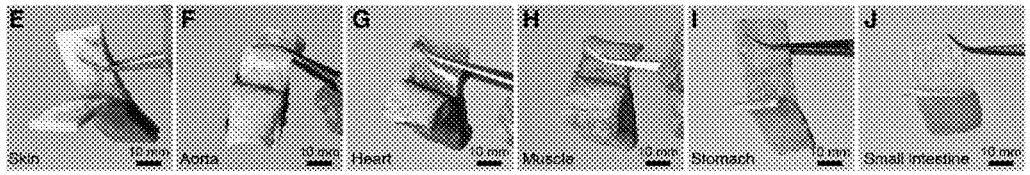
FIG. 14E    FIG. 14F    FIG. 14G    FIG. 14H    FIG. 14I    FIG. 14J

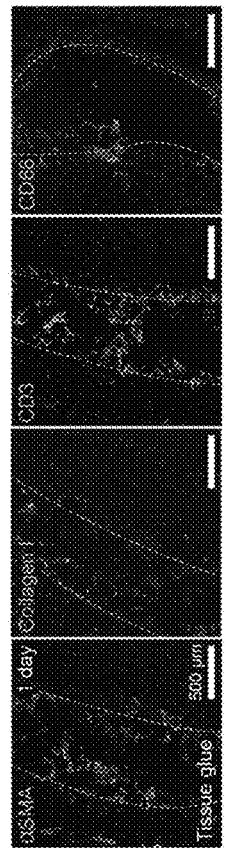
FIG. 18E
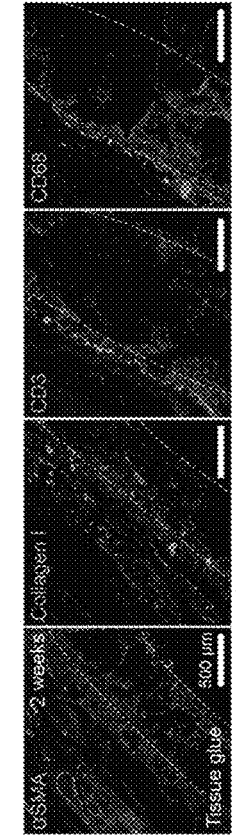
FIG. 18F
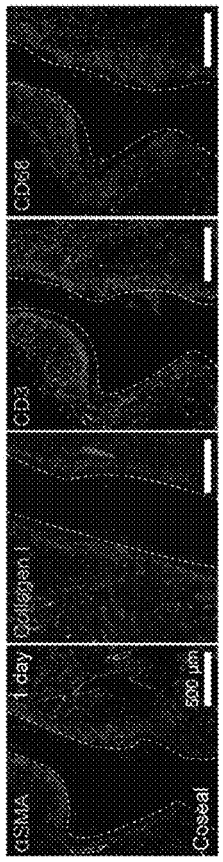
FIG. 18G
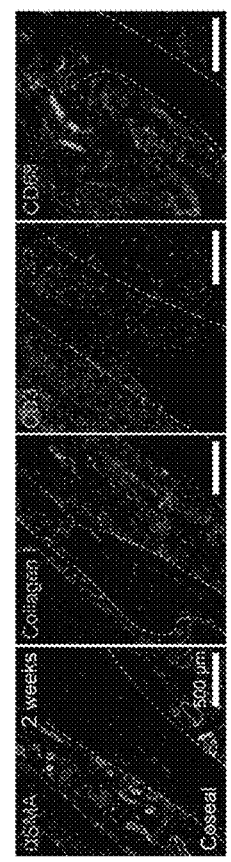
FIG. 18H
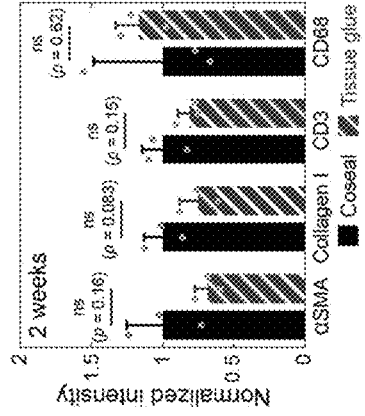
FIG. 18I  FIG. 18J
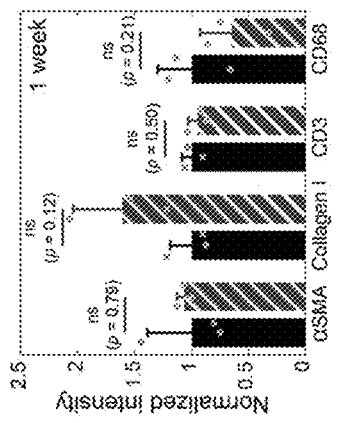
FIG. 18K  FIG. 18L
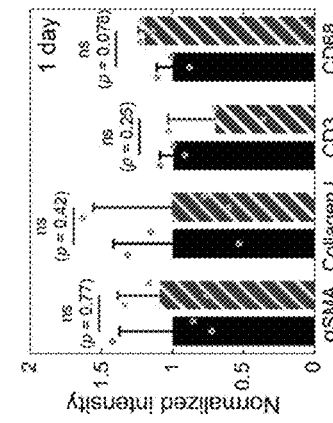

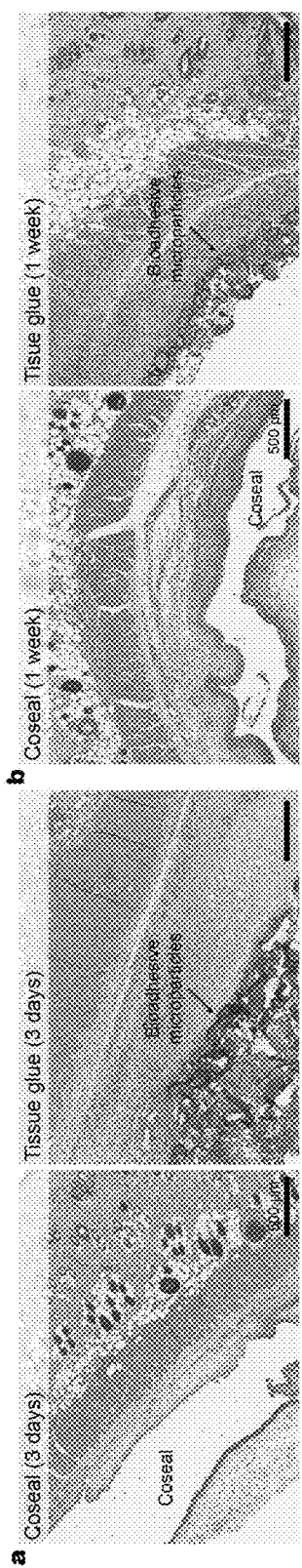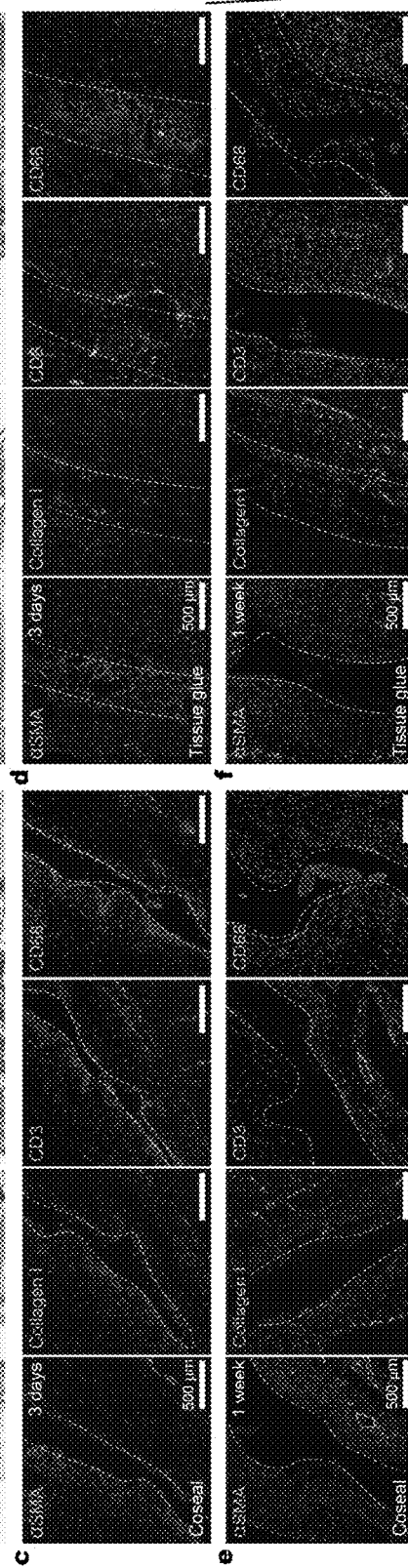
FIG. 19A FIG. 19B FIG. 19C FIG. 19D FIG. 19E FIG. 19F

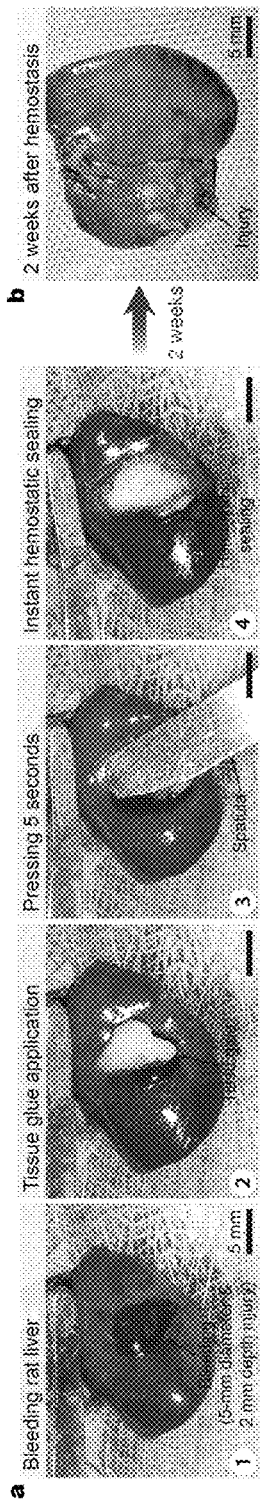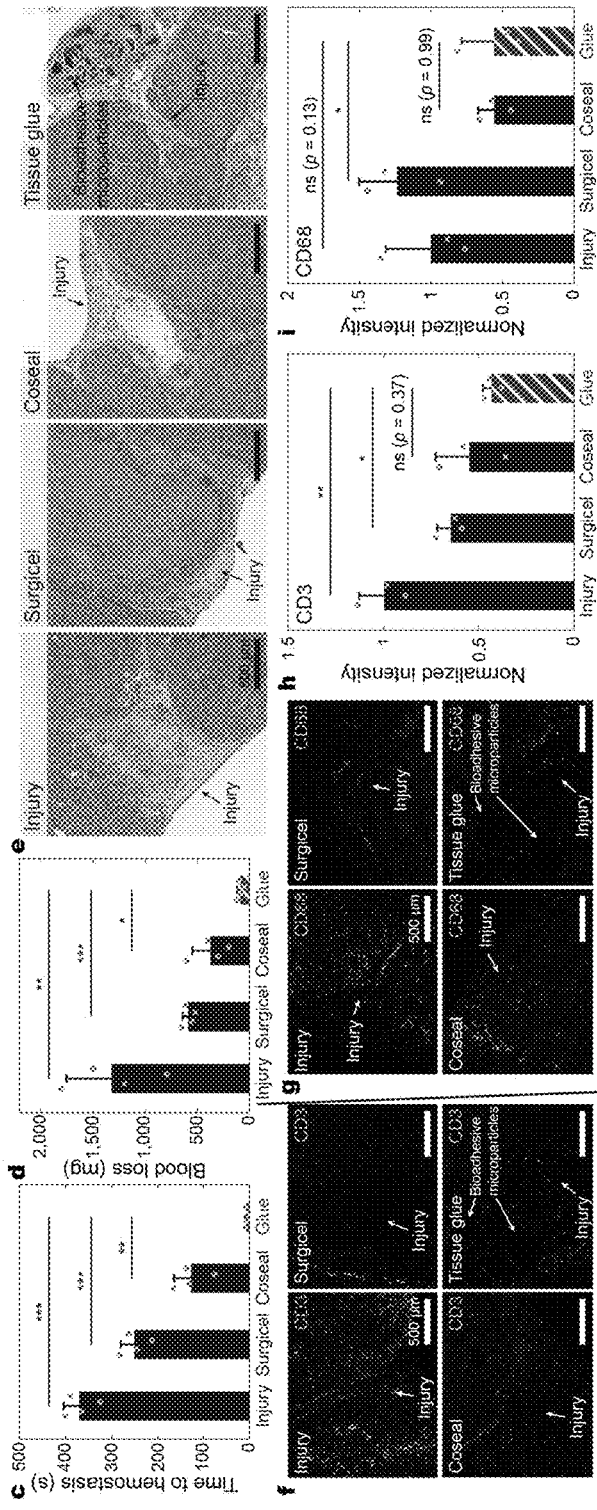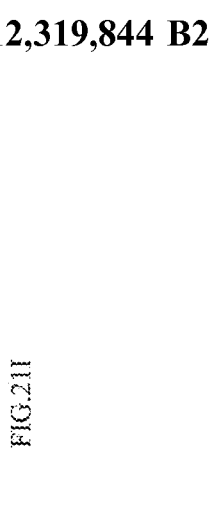

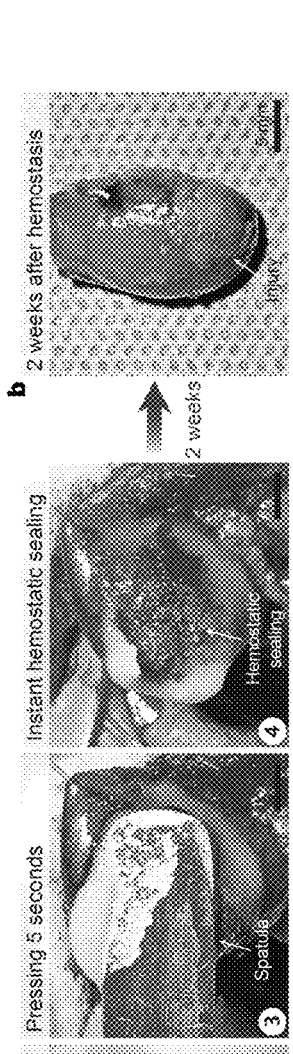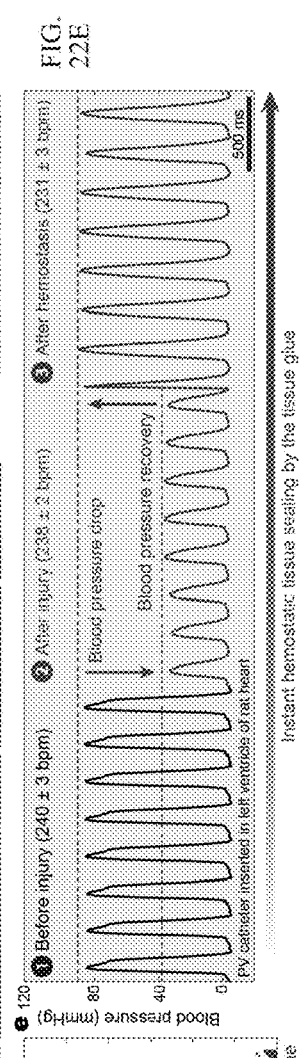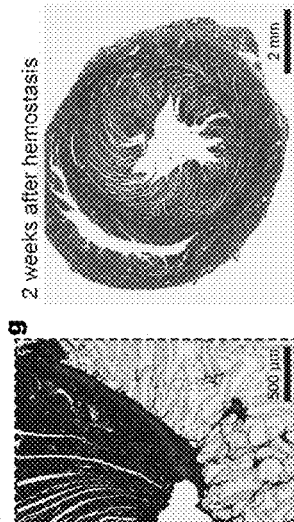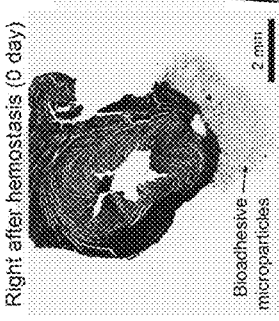
FIG. 22A  FIG. 22B  FIG. 22C  FIG. 22D  FIG. 22E  FIG. 22F  FIG. 22G

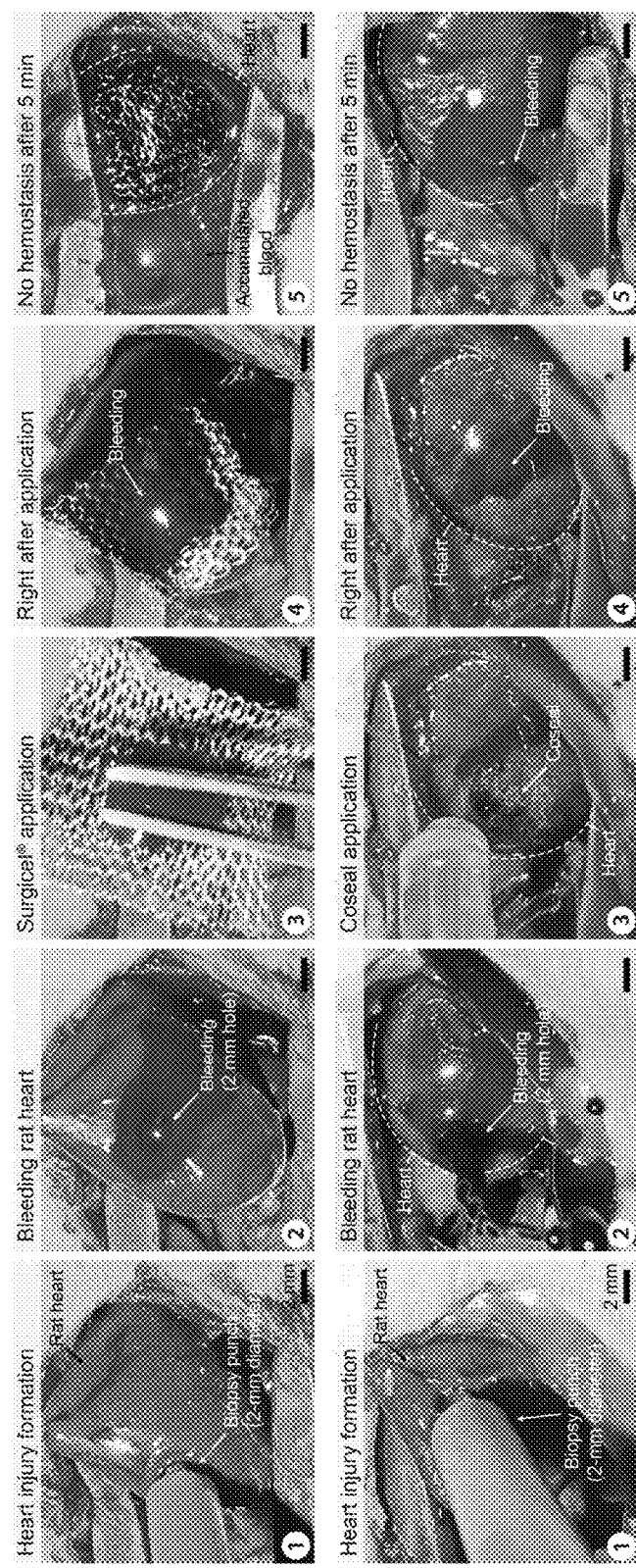

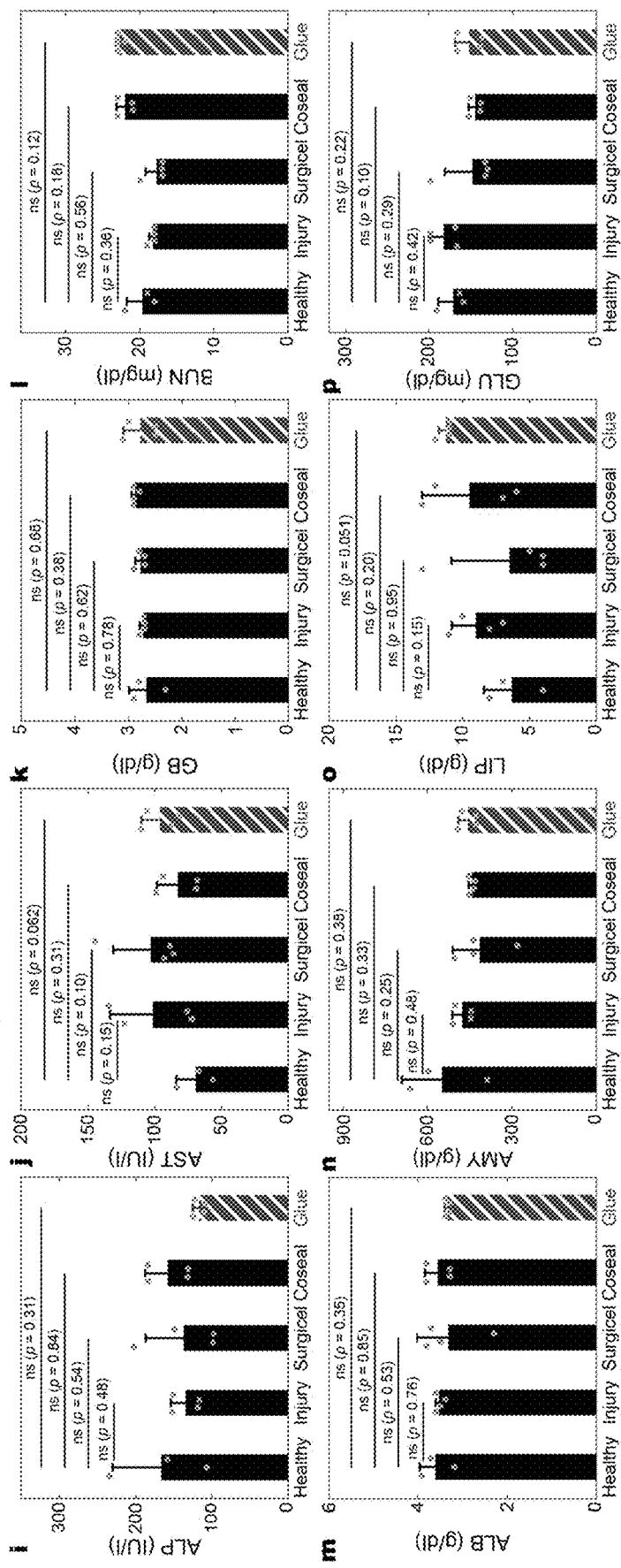

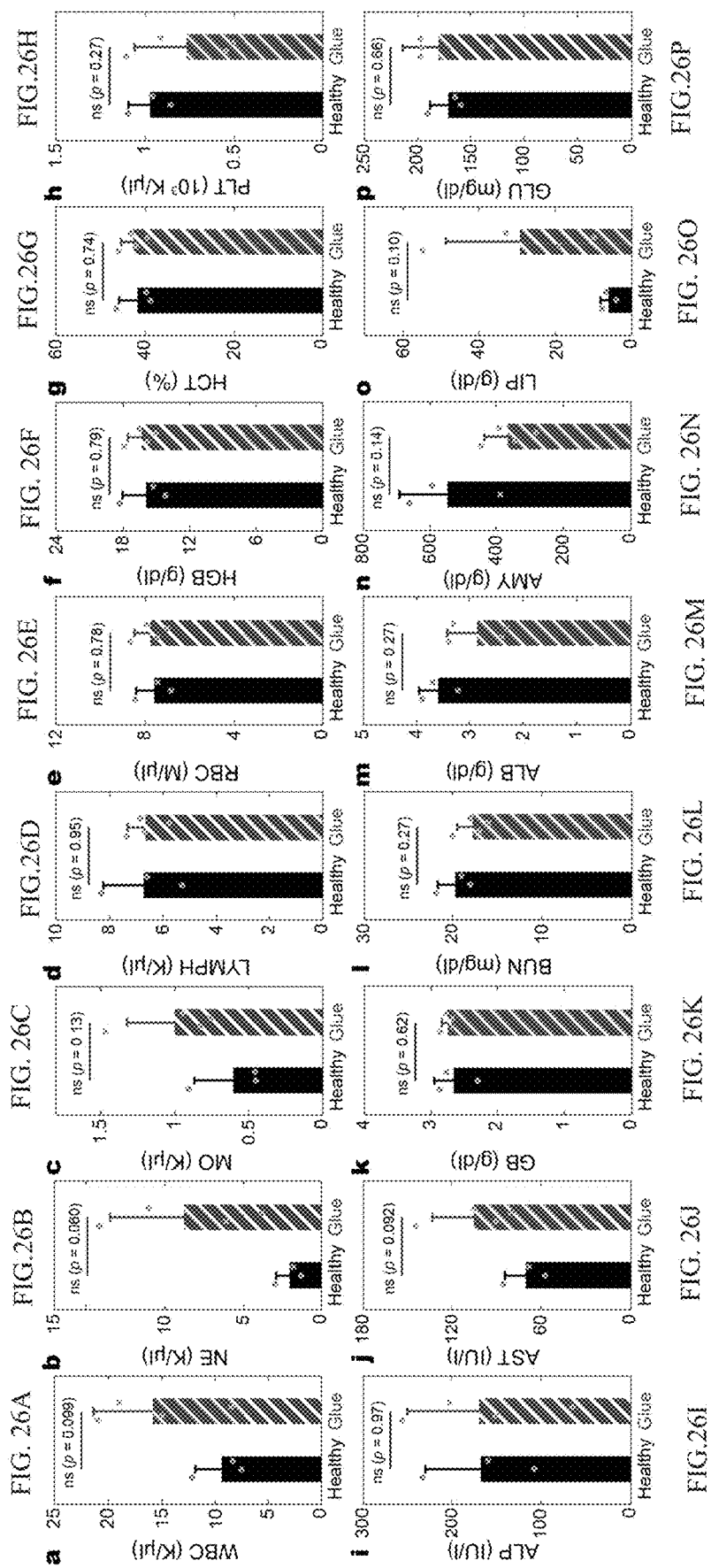

BODY FLUID RESISTANT TISSUE ADHESIVES

CROSS-REFERENCE TO RELATED APPLICATIONS

This divisional application claims benefit to U.S. Non-Provisional patent application Ser. No. 17/110,841, filed Dec. 3, 2020, entitled "Body Fluid Resistant Tissue Adhesives" which claims benefit to U.S. Provisional Patent Application Ser. No. 62/942,874, filed Dec. 3, 2019, entitled "Body Fluid Resistant Tissue Adhesives" which are incorporated by reference herein in its entirety.

GOVERNMENT SUPPORT STATEMENT

This invention was made with Government support under Grant No. CMMI1661627 awarded by the National Science Foundation (NSF), under Grant No. W911NF-13-D-0001 awarded by the Army Research Office (ARO), and under Grant No. N00014-17-1-2920 awarded by the Office of Naval Research (ONR). The Government has certain rights in the invention.

FIELD OF THE INVENTION

The present invention generally relates to an adhesive material and method for adhering tissues, wherein adhesive material is capable of quickly and robustly adhering tissues that are covered in fluid. The adhesive material includes a hydrophobic matrix material with dry bioadhesive microparticles dispersed therein.

BACKGROUND OF THE INVENTION

Traumatic injuries of tissues and organs can be life-threatening yet challenging to treat due to their highly time-sensitive and complex nature (R. R. Rodrigues, M. J. C. Carmona, J. O. C. Junior, Bleeding and damage control surgery. *Current Opinion in Anesthesiology* 29, 229-233 (2016)). For example, uncontrolled hemorrhages following trauma are one of the major causes of mortality in the world costing over two million lives annually (R. Pfeifer, I. S. Tarkin, B. Rocos, H. C. Pape, Patterns of mortality and causes of death in polytrauma patients—has anything changed? *Injury* 40, 907-911 (2009); M. El Sayad, H. Noureddine, Recent advances of hemorrhage management in severe trauma. *Emergency Medicine International* 2014, (2014)). While surgical closure of traumatic injuries is most commonly conducted by sutures or staples following hemostasis, it is challenging to perform this process in a prompt and effective manner after traumatic injuries on site.

While tissue adhesives offer a promising alternative to sutures and staples for wound closure and tissue repair (T. B. Reece, T. S. Maxey, I. L. Kron, A prospectus on tissue adhesives. *The American Journal of Surgery* 182, S40-S44 (2001); P. Coulthard et al., Tissue adhesives for closure of surgical incisions. *Cochrane Database of Systematic Reviews* 5, CD004287 (2010); B. Sharma et al., Human cartilage repair with a photoreactive adhesive-hydrogel composite. *Science Translational Medicine* 5, 167ra166-167ra166 (2013); N. Annabi, K. Yue, A. Tamayol, A. Khademhosseini, Elastic sealants for surgical applications. *European Journal of Pharmaceutics and Biopharmaceutics* 95, 27-39 (2015); E. T. Roche et al., A light-reflecting balloon catheter for atraumatic tissue defect repair. *Science Translational Medicine* 7, 306ra149-306ra149 (2015)), existing tissue adhesives suffer from several limitations. Commercially-available tissue adhesives provide no or only weak and brittle adhesion with tissue surfaces covered by body fluids such as blood and mucus (N. Lang et al., A blood-resistant surgical glue for minimally invasive repair of vessels and heart defects. *Science Translational Medicine* 6, 218ra216-218ra216 (2014); Y. Hong et al., A strongly adhesive hemostatic hydrogel for the repair of arterial and heart bleeds. *Nature Communications* 10, 2060 (2019)). While a few blood-resistant tissue adhesives with improved adhesion performance have been developed, the need for ultraviolet (UV) irradiation and/or prolonged steady pressure application (e.g., over 5 min) to form adhesion substantially limits their utility in practical applications (Lang et al.; Y. Hong et al.; N. Annabi et al., Engineering a highly elastic human protein-based sealant for surgical applications. *Science Translational Medicine* 9, eaai7466 (2017); J. Li et al., Tough adhesives for diverse wet surfaces. *Science* 357, 378-381 (2017)).

Thus, further improvements in both adhesive materials and methods of use are greatly needed.

SUMMARY OF THE INVENTION

The present invention provides a tissue adhesive material that is particularly useful in wet environments. The tissue adhesive material provides fast and robust adhesion even on tissue surfaces covered in bodily fluids and, as such, can provide great benefit in a variety of applications including traumatic injuries requiring fast and reliable wound closure and tissue repair on site.

According to one aspect, the present invention provides an adhesive material for adhering one or more fluid covered surfaces comprising a hydrophobic matrix; and a plurality of bioadhesive microparticles dispersed within the hydrophobic matrix. The bioadhesive microparticles comprise (i) one or more hydrophilic polymers or copolymers, (ii) one or more amine coupling groups, and (iii) one or more cross linkers. The hydrophobic matrix is in the form of a protective matrix around the dispersed bioadhesive microparticles that protects the bioadhesive microparticles from the fluid. The adhesive material is structured such that disposing the adhesive material directly on the fluid covered surface and applying pressure to the adhesive material causes (a) the hydrophobic matrix to repel the fluid, (b) the bioadhesive particles to compress forming an adhesive layer, and (c) the bioadhesive particles to form temporary crosslinks followed by covalent crosslinks with the surface.

Embodiments according to these aspects may include one or more of the following features. The adhesive material is in form of an injectable adhesive material. The one or more hydrophilic polymers or copolymers are selected from hydrophilic polymers or copolymers that absorb water at a dry state. The one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, alginic acid, pectin, and combinations thereof. The one or more amine coupling groups are selected from N-hydroxysuccinimide ester, N-hydroxysulfosuccinimide ester, aldehyde, imidoester, epoxide, isocyanate, catechol, and combinations thereof. The one or more cross-linkers are selected from gelatin methacrylate, hyaluronic acid methacrylate, oxidized methacrylic alginate, polycaprolactone diacrylate, N,N'-bis(acryloyl) cystamine, N,N'- methylenebis(acrylamide), polyethylene glycol diacrylate, polyethylene glycol dimethacrylate, and combinations thereof. The hydrophobic matrix is selected from silicone oils, mineral oils, essential oils, perfluoropolyether oils, lanolin oils, and combinations thereof. The adhesive material comprises the plurality of bioadhesive microparticles fabricated of (i) poly(acrylic acid) grafted with (ii) N-hydroxysuccinimide ester (PAAc-co-NHS ester) (iii) crosslinked with biodegradable gelatin methacrylate and (i) biodegradable chitosan, dispersed in a silicone oil hydrophobic matrix. The adhesive material is biocompatible. The adhesive material adheres with an interfacial toughness of at least about 100 J m$^{-2}$, shear strength of at least about 30 kPa and tensile of at least about 10 kPa. The bioadhesive microparticles contain carboxylic acid groups which form the temporary crosslinks by intermolecular bonds, and the amine coupling groups form the covalent crosslinks with the surface. The bioadhesive microparticles have a particle size ranging from about 10 μm to about 200 μm. A ratio between the bioadhesive microparticles and the hydrophobic matrix ranges from about 1:3 to about 1:0.5. The one or more fluids are physiological body fluids selected from blood, saliva, gastrointestinal fluid, mucus, succus, and combinations thereof. The adhesive material is biodegradable and is configured to allow cell infiltration into the crosslinked bioadhesive microparticles and healing of an underlying tissue injury. Healing of an underlying tissue injury comprises tissue cells replacing the biodegrading bioadhesive microparticles to heal an underlying tissue injury.

According to another aspect, the present invention provides a method of adhering one or more tissue surfaces covered in one or more fluids comprising: (a) applying an adhesive material directly to one or more of the fluid covered tissue surfaces, the adhesive material comprising: a hydrophobic matrix; and a plurality of bioadhesive microparticles dispersed within the hydrophobic matrix, the bioadhesive microparticles comprising: (i) one or more hydrophilic polymers or copolymers; (ii) one or more amine coupling groups, and (iii) one or more cross linkers; (b) applying pressure ranging from about 1 kPa to 50 kPa to the adhesive material; (c) allowing the hydrophobic matrix to repel and clean the one or more fluids from the tissue surfaces; (d) allowing physical bond forming group in the bioadhesive microparticles to form temporary crosslinks by intermolecular bonds; and (e) allowing amine coupling groups in the bioadhesive microparticles to form covalent crosslinks with the tissue surfaces.

Embodiments according to these aspects may include one or more of the following features. Pressure is applied for about 5 seconds to about 30 seconds. The adhesive material is an injectable adhesive material, and the adhesive material is applied using a syringe. The one or more hydrophilic polymers or copolymers are selected from hydrophilic polymers or copolymers that absorb water at dry state. The one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, alginic acid, pectin, and combinations thereof. The one or more amine coupling groups are selected from N-hydroxysuccinimide ester, N-hydroxysulfosuccinimide ester, aldehyde, imidoester, epoxide, isocyanate, catechol, and combinations thereof. The one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The hydrophobic matrix is selected from silicone oils, mineral oils, essential oils, perfluoropolyether oils, lanolin oils, and combinations thereof. The adhesive comprises plurality of bioadhesive microparticles are fabricated of (i) poly(acrylic acid) grafted with (ii) N-hydroxysuccinimide ester (PAAc-co-NHS ester) (iii) crosslinked with biodegradable gelatin methacrylate and (i) biodegradable chitosan, dispersed in a silicone oil hydrophobic matrix. The adhesive material adheres with an interfacial toughness of at least about 100 J m$^{-2}$, shear strength of at least about 30 kPa and tensile of at least about 10 kPa. The physical bond forming groups in the bioadhesive microparticles are carboxylic acid groups which form the temporary crosslinks by intermolecular bonds. The bioadhesive microparticles have a particle size ranging from about 10 μm to about 200 μm. The adhesive material comprises a ratio between the bioadhesive microparticles and the hydrophobic matrix ranging from about 1:3 to about 1:0.5. The one or more fluids are physiological body fluids selected from blood plasma, interstitial fluid, lymphatic fluid, cerebrospinal fluid, gastrointestinal fluid, and combinations thereof. After (a) applying an adhesive material directly to one or more of the fluid covered tissue surfaces and prior to (b) applying pressure, the method further comprises applying a backing material to the adhesive material and wherein (b) applying pressure comprises applying pressure to the adhesive material via the backing material. The backing material is fabricated of a biocompatible material that does not adhere to wet surfaces. The backing material is fabricated of oxidized cellulose, silicone elastomer, polyurethane, hydrogel, any other biocompatible materials that do not adhere to wet tissue, and combinations thereof. The one or more tissue surfaces can comprise a tissue injury, and the method further comprises allowing cell infiltration into the crosslinked bioadhesive microparticles and healing of the underlying tissue injury.

According to another aspect, the present invention provides a method of healing a tissue injury comprising (a) applying an adhesive material directly to the tissue injury, wherein the tissue injury comprises one or more fluid covered tissue surfaces, the adhesive material comprising: a hydrophobic matrix; and a plurality of bioadhesive microparticles dispersed within the hydrophobic matrix, the bioadhesive microparticles comprising: (i) one or more hydrophilic polymers or copolymers; (ii) one or more amine coupling groups, and (iii) one or more cross linkers; (b) applying pressure ranging from about 1 kPa to 50 kPa to the adhesive material; (c) allowing the hydrophobic matrix to repel and clean the one or more fluids from the tissue surfaces; (d) allowing physical bond forming group in the bioadhesive microparticles to form temporary crosslinks by intermolecular bonds; (e) allowing amine coupling groups in the bioadhesive microparticles to form covalent crosslinks with the tissue surfaces; and (f) allowing cell infiltration into the crosslinked bioadhesive microparticles and healing of the underlying tissue injury.

Embodiments according to these aspects may include one or more of the following features. The adhesive material is biodegradable, and the cells replace the biodegrading bioadhesive microparticles to heal the underlying tissue injury. Pressure is applied for about 5 seconds to about 30 seconds. The adhesive material is an injectable adhesive material, and the adhesive material is applied using a syringe. The one or more hydrophilic polymers or copolymers are selected from hydrophilic polymers or copolymers that absorb water at dry state. The one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, alginic acid, pectin, and combinations thereof. The one or more amine coupling groups are selected from N-hydroxysuccinimide ester, N-hydroxysulfosuccinimide ester, aldehyde, imidoester, epoxide, isocyanate, catechol, and combinations thereof. The one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The hydrophobic matrix is selected from silicone oils, mineral oils, essential oils, perfluoropolyether oils, lanolin oils, and combinations thereof. The adhesive comprises plurality of bioadhesive microparticles are fabricated of (i) poly(acrylic acid) grafted with (ii) N-hydroxysuccinimide ester (PAAc-co-NHS ester) (iii) crosslinked with biodegradable gelatin methacrylate and (i) biodegradable chitosan, dispersed in a silicone oil hydrophobic matrix. The adhesive material adheres with an interfacial toughness of at least about 100 J m$^{-2}$, shear strength of at least about 30 kPa and tensile of at least about 10 kPa. The physical bond forming groups in the bioadhesive microparticles are carboxylic acid groups which form the temporary crosslinks by intermolecular bonds. The bioadhesive microparticles have a particle size ranging from about 1am to about 200 μm. The adhesive material comprises a ratio between the bioadhesive microparticles and the hydrophobic matrix ranging from about 1:3 to about 1:0.5. The one or more fluids are physiological body fluids selected from blood plasma, interstitial fluid, lymphatic fluid, cerebrospinal fluid, gastrointestinal fluid, and combinations thereof. After (a) applying an adhesive material directly to one or more of the fluid covered tissue surfaces and prior to (b) applying pressure, the method further comprises applying a backing material to the adhesive material and wherein (b) applying pressure comprises applying pressure to the adhesive material via the backing material. The backing material is fabricated of a biocompatible material that does not adhere to wet surfaces. The backing material is fabricated of oxidized cellulose, silicone elastomer, polyurethane, hydrogel, any other biocompatible materials that do not adhere to wet tissue, and combinations thereof.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIGS. 1A-C schematically illustrate the tissue adhesive material according to an embodiment of the present invention, wherein FIG. 1A shows the adhesive material formed of dry bioadhesive microparticles and a hydrophobic oil matrix deposited on a tissue covered in body fluids, FIGS. 1B-C show the repel-crosslinking mechanism in which the adhesive material repels body fluids (FIG. 1B) and forms robust adhesion by crosslinking (FIG. 1C), and FIGS. 1D-E photographically depict the adhesive material injected on blood-covered porcine skin tissue (FIG. 1D), pressed by a gelatin-coated glass substrate (FIG. 1E), and adhered on the tissue surface (FIG. 1F), FIGS. 1D-E corresponding to each panel in FIGS. 1A-C, respectively.

FIGS. 3A-E show photographs illustrating the preparation of a tissue adhesive material according to an embodiment of the present invention, wherein FIG. 3A shows small cut pieces of dry bioadhesive, FIG. 3B shows addition of the dry bioadhesive to a stainless steel container with stainless steel balls, FIG. 3C shows use of a cryogenic ball mill to grind the dry bioadhesive, FIG. 3D shows the resulting dry bioadhesive microparticles, and FIG. 3E shows the tissue adhesive material (dry bioadhesive microparticles mixed with hydrophobic matrix) delivered through a syringe.

FIG. 4 schematically illustrate an overall process of a tissue adhesive application according to an embodiment of the present invention, where the adhesive is applied directly on tissue surfaces covered by body fluids, followed by application of gentle pressure which causes (i) the hydrophobic matrix to repel and clean body fluids from the tissue surface and simultaneously (ii) physical bond forming groups in the bioadhesive microparticles temporarily crosslinked by intermolecular bonds, followed by covalent crosslinking where the swollen and crosslinked tissue adhesive material forms a thin layer of hydrogel which provides robust adhesion between the tissues.

FIGS. 8A-J illustrate SEM images of varying dry bioadhesive micro particle size by cryogenic grinding for 2 min under various grinding frequency (8A, 8C, 8E, 8G, 8I) and tissue adhesive injectability via a syringe with 2.5-mm or 1.2-mm diameter using these varying dry bioadhesive micro particle sizes (8B, 8D, 8F, 8H, 8J), wherein FIG. 8A-B correspond to 10 Hz and 2.5-mm diameter syringe, FIG. 8C-D corresponding to 15 Hz and 1.2-mm diameter syringe, FIG. 8E-F correspond to 20 Hz and 1.2-mm diameter syringe, FIG. 8F-G correspond to 25 Hz and 1.2-mm diameter syringe, and FIG. 8H-I correspond to 30 Hz and 1.2-mm diameter syringe.

FIGS. 10A-E schematically and graphically illustrate the effects of matrix materials in the tissue adhesive, wherein FIG. 10A schematically illustrate of the setup and procedure for pull-off tests, FIG. 10B graphically shows pull-off forces using dry bioadhesive microparticles without and with a hydrophobic matrix (silicone oil) measured in a PBS bath, FIG. 10C graphically illustrates pull-off forces using dry bioadhesive microparticles without and with a silicone oil matrix measured in a porcine blood bath, FIG. 10D schematically illustrates configurations for the tissue adhesive and corresponding total surface energies, and FIG. 10E graphically illustrates pull-off forces vs. applied pressure between two tissues adhered by dry bioadhesive microparticles with varying viscosity silicone oil matrices ($\eta_m$=5 cSt or 100 cSt) measured in porcine blood bath. Vertical dashed lines indicate threshold applied pressures. Error bars indicate SD; N=5. P values are determined by a Student's t test; ***$p \leq 0.001$.

FIGS. 13A-C schematically illustrate the mechanical testing setups (for the measurement of adhesion performance, wherein FIG. 13A illustrates the standard 180-degree peel test (ASTM F2256), FIG. 13B illustrates the testing setup for shear strength measurements based on the standard lap-shear test (ASTM F2255), and FIG. 13C illustrates the testing setup for tensile strength measurements based on the standard tensile test (ASTM F2258), with graphical and photographic results also depicted.

FIGS. 14A-J illustrate the adhesion performance of tissue adhesive according to an embodiment of the present invention, wherein FIG. 14A graphically depicts interfacial toughness vs. pressing time for adhered blood-covered porcine skin tissues, FIG. 14B graphically depicts interfacial toughness vs. storage time for adhered blood-covered porcine skin tissues, FIG. 14C graphically compares adhesion performances between the tissue adhesive and various commercially-available tissue adhesives and glues on blood-covered porcine skin tissues, FIG. 14D graphically compares interfacial toughness and shear and tensile strength between various blood- or mucus-covered tissues adhered by the tissue adhesive, and FIGS. 14E-J photographically illustrate various blood- or mucus-covered tissues adhered by the tissue adhesive, where all samples were kept in wet environment before the mechanical tests. Error bars indicate SD; N=3 to 5. Statistical significance and p values are determined by one-way ANOVA and Tukey's multiple comparison test; ns, not significant.

FIGS. 16A-B illustrate a potential application of the tissue adhesive according to an embodiment of the present invention, wherein FIG. 16A illustrates instant hemostatic sealing of a bleeding ex vivo porcine aorta by the tissue adhesive with a Surgicel® backing, and FIG. 16B graphically compares burst pressure on a blood-covered porcine aorta using the tissue adhesive, sutures, Surgiflo, and Tisseel. Error bars indicate SD; N=3.

FIGS. 18A-K illustrate the biocompatibility of the tissue adhesive according to an embodiment of the present invention, wherein FIG. 19A shows in vitro cell viability of rat cardiomyocytes based on LIVE/DEAD assay after 24-h culture in control media (DMEM), Coseal-incubated media, and the present invention tissue adhesive-incubated media (bottom-right panel). Representative confocal images of the LIVE/DEAD assay for control (top-left panel), Coseal (top-right panel), and the tissue glue (bottom-left panel). DMEM, Dulbecco's Modified Eagle Medium, FIGS. 18B-C show representative histology images stained with hematoxylin and eosin (H&E) for Coseal and the tissue glue after rat subcutaneous implantation for 1 day (FIG. 18B) and 2 weeks (FIG. 18C). 4 independent experiments were conducted with similar results, FIG. 18C illustrates the degree of inflammation evaluated by a blinded pathologist (0, normal; 1, very mild; 2, mild; 3, severe; 4, very severe), FIGS. 18E-H show representative immunofluorescence images of Coseal (FIG. 18E) and the present invention tissue adhesive (FIG. 18F) after rat subcutaneous implantation for 1 day; Coseal (FIG. 18G) and the present invention tissue adhesive (FIG. 18H) after rat subcutaneous implantation for 2 weeks (cell nuclei are stained with 4',6-diamidino-2-phenylindole (DAPI, Blue); green fluorescence corresponds to the expression of fibroblast (aSMA), type 1 collagen (Collagen-I), T-cell (CD3), and macrophage (CD68), respectively), FIGS. 18I-L illustrate normalized fluorescence intensity from the immunofluorescence images for Coseal and the tissue glue after rat subcutaneous implantation for 1 day (FIG. 18I), 3 days (FIG. 18K), 1 week (FIG. 18K), and 2 weeks (FIG. 18L). Values in FIGS. 18A, D, I-L represent the mean and the standard deviation (n=4 independent samples). Statistical significance and p values are determined by two-sided Student t-5 test; ns, not significant; *$p < 0.05$.

FIGS. 19A-F illustrate the histology and immunofluorescence images of subcutaneous implants, wherein FIGS. 19A-B show representative histology images stained with hematoxylin and eosin (H&E) for Coseal and the present invention tissue adhesive after rat subcutaneous implantation for 3 days (FIG. 19A) and 1 week (FIG. 19B), where 4 independent experiments were conducted with similar results, FIGS. 19C-F illustrate representative immunofluorescence images of Coseal (c) and the tissue glue (d) after rat subcutaneous implantation for 3 days; Coseal (e) and the tissue glue (f) after rat subcutaneous implantation for 1 week. Cell nuclei are stained with 4',6-diamidino-2-phenylindole (DAPI, Blue). Green fluorescence corresponds to the expression of 15 fibroblast (αSMA), type 1 collagen (Collagen-I), T-cell (CD3), and macrophage (CD68), respectively.

FIGS. 20A-C show representative histology images stained with hematoxylin and eosin (H&E) for the tissue adhesive after rat subcutaneous implantation for 2 weeks (FIG. 20A), 4 weeks (FIG. 20B), and 8 weeks (FIG. 20C), where 4 independent experiments were conducted with similar results, and FIG. 20D shows a representative histology image stained with hematoxylin and eosin (H&E) for a gelatin-based tissue adhesive after rat subcutaneous implantation for 2 weeks, where 4 independent experiments were conducted with similar results.

FIGS. 21A-I illustrate the instant hemostatic sealing of a liver by the present invention tissue adhesive according to embodiments of the present invention, where FIG. 21A shows instant hemostatic sealing of a bleeding rat liver in vivo by the tissue adhesive, FIG. 21B shows an excised rat liver 2 weeks after hemostatic sealing by the tissue adhesive, FIGS. 21C-D show time to hemostasis (FIG. 21C) and blood loss until hemostasis (FIG. 21D) for hepatic bleeding without treatment (injury), Surgicel, Coseal, and the tissue adhesive, FIG. 21E shows representative histology images stained with hematoxylin and eosin (H&E) for injured liver without treatment (injury) and hemostatic sealing formed by Surgicel, Coseal, and the present invention tissue adhesive 2 weeks after hemostasis, where 4 independent experiments were conducted with similar results, FIGS. 21F-G show representative immunofluorescence images for an injured liver without treatment (injury) and with hemostatic sealing by Surgicel, Coseal, and the present invention tissue adhesive 2 weeks after hemostasis (cell nuclei were stained with 4',6-diamidino-2-phenylindole (DAPI, Blue), green fluorescence corresponds to the expression of T-cell (CD3, f) and macrophage (CD68, g), respectively), FIGS. 21H-I show normalized fluorescence intensity from the immunofluorescence images for CD3 (FIG. 21H) and CD68 (FIG. 21I). Values in FIG. 21C, D, H, I represent the mean and the standard deviation (n=4 independent samples). Statistical significance and p values were determined by two-sided Student t-test; ns, not significant; *$p \leq 150.05$; $p \leq 0.01$; *$p \leq 0.001$.

FIGS. 22A-G illustrate the instant hemostatic sealing of a heart using the present invention tissue adhesive according to embodiments of the present invention, where FIG. 22A illustrates the instant hemostatic sealing of a bleeding rat heart in vivo by the tissue adhesive, FIG. 22B shows an excised rat heart 2 weeks after hemostatic sealing by the tissue adhesive, FIGS. 22C-D show the time to hemostasis (FIG. 22C) and blood loss until hemostasis (FIG. 22D) for cardiac bleeding without treatment (injury), Surgicel, Coseal, and the present invention tissue adhesive, FIG. 22E shows intraventricular blood pressure and heart rate of a rat heart before injury, after injury (2-mm biopsy punch), and after hemostatic sealing by the present invention tissue adhesive, FIGS. 22F-G show representative histology images stained with Masson's trichrome for an injured heart with hemostatic sealing by the present invention tissue adhesive right after (FIG. 22F) and 2 weeks after (FIG. 22G) hemostasis, where 4 independent experiments were conducted with similar results. Values in FIGS. 22C-D represent the mean and the standard deviation (n=4 independent samples). Statistical significance and p values are determined by one-way ANOVA and Tukey's multiple comparison test; $p \leq 0.01$; *$p \leq 0.001$.

FIG. 23A shows hemostatic sealing of a bleeding rat liver in vivo by Surgicel, FIG. 23B shows an excised rat liver 2 weeks after hemostatic sealing by Surgicel, FIG. 23C shows hemostatic sealing of a bleeding rat liver in vivo by Coseal, and FIG. 23D shows an excised rat liver 2 weeks after hemostatic sealing by Coseal.

FIGS. 24A-B illustrates hemostatic sealing of a heart by commercially-available products, where FIG. 24A shows hemostatic sealing of a bleeding rat heart in vivo by Surgicel and FIG. 24B shows hemostatic sealing of a bleeding rat heart in vivo by Coseal.

FIGS. 25A-P graphically illustrate blood analysis of animals with hemostatic sealing of liver, with FIGS. 25A-H showing complete blood count (CBC) of the healthy animals and the animals 2 weeks after hemostatic sealing of liver for white blood cell (WBC, FIG. 25A), neutrophil (NE, FIG. 25B), monocyte (MO, FIG. 25C), lymphocyte (LYMPH, FIG. 25D), red blood cell (RBC, FIG. 25E), hemoglobin (HGB, FIG. 25F), hematocrit (HCT, FIG. 25G), and platelet (PLT, FIG. 25H), FIGS. 25I-P show blood chemistry of the healthy animals and the animals 2 weeks after hemostatic sealing of liver for alkaline phosphatase (ALP, FIG. 25I), aspartate transaminase (AST, FIG. 25J), globulin (GB, FIG. 25K), blood urea nitrogen (BUN, FIG. 25L), albumin (ALB, FIG. 25M), amylase (AMY, FIG. 25N), lipase (LIP, FIG. 25O), and glucose (GLU, FIG. 25P). Values represent the mean and the standard deviation (n=4 independent samples). Statistical significance and p values are determined by two-sided Student t-test; ns, not significant; *$p \leq 10\ 0.05$.

FIGS. 26A-P graphically illustrate blood analysis of the animals with hemostatic sealing of heart, where FIGS. 26A-H show complete blood count (CBC) of the healthy animals and the animals 2 weeks after hemostatic sealing of heart for white blood cell (WBC, FIG. 26A), neutrophil (NE, FIG. 26B), monocyte (MO, FIG. 26C), lymphocyte (LYMPH, FIG. 26D), red blood cell (RBC, FIG. 26E), hemoglobin (HGB, FIG. 26F), hematocrit (HCT, FIG. 26G), and platelet (PLT, FIG. 26H), FIGS. 26I-P show blood chemistry of the healthy animals and the animals 2 weeks after hemostatic sealing of heart for alkaline phosphatase (ALP, FIG. 26I), aspartate transaminase (AST, FIG. 26J), globulin (GB, FIG. 26K), blood urea nitrogen (BUN, FIG. 26L), albumin (ALB, FIG. 26M), amylase (AMY, FIG. 26N), lipase (LIP, FIG. 26O), and glucose (GLU, FIG. 26P). Values represent the mean and the standard deviation (n=4 independent samples). Statistical significance and p values are determined by two-sided Student t-test; ns, not significant.

DETAILED DESCRIPTION

Figure 2A:
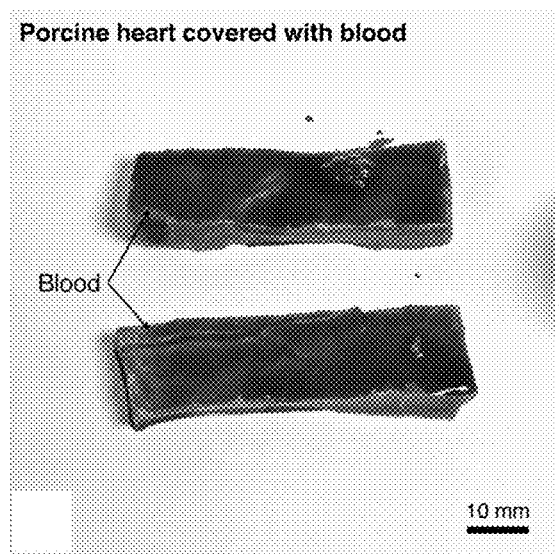
FIGS. 2A-D show photographs in which two porcine heart tissues covered with blood are quickly and robustly adhered using the tissue adhesive according to an embodiment of the present invention, after applying gentle pressure for 5 sec.
Figure 2B:
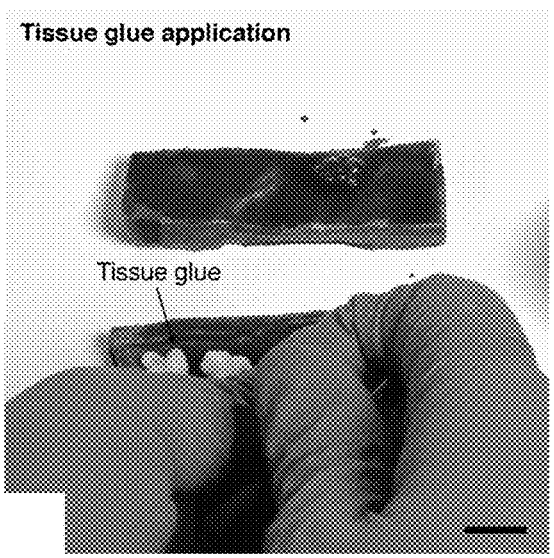
Figure 2C:
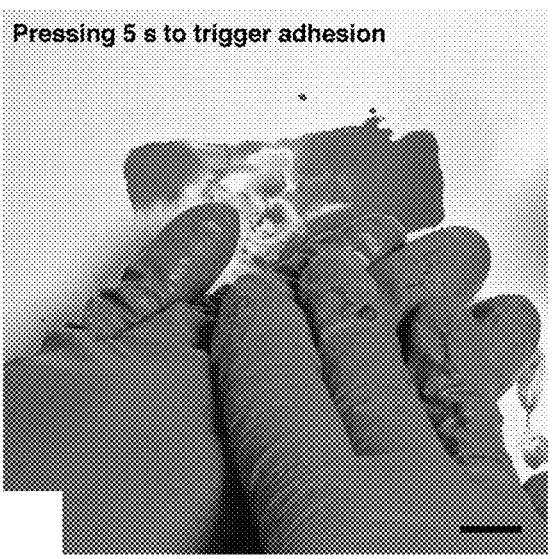

The following definitions are useful for interpreting terms applied to features of the embodiments disclosed herein, and are meant only to define elements within the disclosure.

As used herein, the term "tough", when describing the adhesion formed by the tissue adhesive, refers to an interfacial toughness of at least about 100 J m$^{-2}$, 120 J m$^{-2}$, 140 J m$^{-2}$, 160 J m$^{-2}$, 180 J m$^{-2}$, 200, J m$^{-2}$, 220 J m$^{-2}$, 240 J m$^{-2}$, at least about 250 J m$^{-2}$, at least about 260 J m$^{-2}$, at least about 270 J m$^{-2}$, at least about 280 J m$^{-2}$, at least about 290 J m$^{-2}$, and even values of at least about 300 J m$^{-2}$.

As used herein, the term "strong", when describing the adhesion formed by the tissue adhesive, refers to a shear or tensile strengths of at least about 10 kPa, at least about 20 kPa, at least about 30 kPa, at least about 40 kPa, at least about 50 kPa, at least about 60 kPa, and at least about 70 kPa.

As used herein, the term "robust", when describing the adhesion formed by the tissue adhesive, refers collectively to the toughness and strength of the adhesion, including measurements of interfacial toughness over 100 J m$^{-2}$, shear strength over 30 kPa, and tensile strength over 10 kPa, and in a preferred embodiment, an interfacial toughness of at least about 240 J m$^{-2}$, shear strength of at least about 70 kPa and tensile of at least about 50 kPa.

As used herein, the term "instant" and "fast", when used to describe the instant/fast adhesion provided by the tissue adhesive, refers to a time of 30 seconds or less, more preferably seconds or less, more preferably 20 seconds or less, more preferably 15 seconds or less, more preferably 10 seconds or less, more preferably 9 seconds or less, more preferably 8 seconds or less, more preferably 7 seconds or less, more preferably 6 seconds or less, and even more preferably 5 seconds or less. This time is measured from the instant that the tissue adhesive is applied to the tissue surface and gentle pressure applied to the time that the bioadhesive microparticles within the tissue adhesive crosslink with the surface to form robust adhesion. The formation of the adhesion can be experimentally determined by a simple pulling test and visual inspection, wherein the adhered tissues do not separate when pulled.

As used herein, the term "gentle", when used to describe the pressure applied to the adhesive material, refers to a pressure of no greater than about 50 kPa, for example ranging from about 1 kPa to about 50 kPa. For example, a gentle pressure would refer to a pressure of no greater than about 45 kPa, no greater than about 40 kPa, no greater than about 35 kPa, no greater than about 30 ka, no greater than about 25 kPa, no greater than about 20 kPa, no greater than about 15 kPa, no greater than about 10 kPa, no greater than about 8 kPa, no greater than about 6 kPa, no greater than about 5 kPa, no greater than about 4 kPa, no greater than about 3 kPa, no greater than about 2 kPa, and even as low as about 1 kPa. According to an exemplary embodiment, a suitable gentle pressure is about 10 kPa.

As used herein, the term "covered", when used to describe the surface to which the adhesive material is applied as being "covered" with fluid, refers to a surface that is partially or completely covered with fluid. As such, "covered" can include a configuration in which an entire layer of fluid is disposed on the surface that the adhesive material is applied to such that, upon application of the adhesive material and prior to repelling of the fluid, a layer of fluid separates the entire adhesive material from the surface. "Covered" can also include a configuration in which only a portion (less than 100% but greater than 50%) of a surface to which the adhesive material is applied has a layer of fluid disposed therein, such that one or more portions of the adhesive material are separated from the surface by the fluid and one or more portions of the adhesive material are in direct contact with the surface prior to repelling of the fluid.

As used herein, the term "dry" when describing the bioadhesive microparticles of the present invention refers to a material that is below the equilibrium moisture content of the material in use. As such, when dry bioadhesive microparticles of the present invention is placed in contact with a wet tissue or other wet or wetted (e.g., wetted by saline) surface to which it will adhere, the material will absorb water, saline, moisture, interstitial fluid, and intracellular fluid from the wet or wetted surface. Generally, dry bioadhesive microparticles will have less than about 50% by weight of liquid components based on total weight of the dry bioadhesive microparticles.

As used herein, the term "body fluid" refers to aqueous physiological fluids including blood, saliva, gastrointestinal fluid, mucus, and succus.

As used herein, the term "wet tissue" refers to the biological tissues that contain with aqueous media including water, saline, interstitial fluid, and intracellular fluid.

As used herein, the term "absorb" when describing the mechanism by which the dry bioadhesive microparticles absorb aqueous media including water, saline, moisture, interstitial fluid, and intracellular fluid from a wet tissue surface in which it is placed in contact with, refers to atoms or molecules from the liquid of the wet surface crossing the surface of and entering the dry bioadhesive microparticles.

As used herein, the term "bioadhesive" when used to describe the dry bioadhesive microparticles refers the capability of the material to form adhesion on the surface of biological tissues.

As used herein, the term "microparticle" when used to describe the dry bioadhesive microparticles refers to a particulate form of the material with the average diameter no greater than about 200 μm, for example any value ranging from about 5 μm to about 200 μm. For example, the term microparticle may refer to a particulate form of the material with an average diameter of no greater than about 180 μm, no greater than about 160 μm, no greater than about 140 μm, no greater than about 120 μm, no greater than about 140 μm, no greater than about 120 lam, no greater than about 100 μm, no greater than about 80 μm, no greater than about 60 μm, no greater than about 40 μm, no greater than about 20 μm, and no greater than about 10 μm. However, any particle size ranging from about 5 μm to about 200 μm could be suitably selected depending upon the ultimate use of the adhesive material, and other factors such as desired rheological properties of the adhesive material. According to an exemplary embodiment, a suitable microparticle has size about 10 μm.

As used herein, the term "temporary" when used to describe the temporary crosslinks formed by the bioadhesive microparticles refers to physical bond forming groups such as carboxylic acid groups in the bioadhesive microparticles forming temporary crosslinks by intermolecular bonds, and refers to a time range extending between time at which the instant temporary crosslinks form and the time in which stable covalent crosslinking is formed between amine-coupling groups such as NHS ester groups and the primary amine groups with themselves and with the adhered surfaces.

As used herein, "swelling" when used to describe the dry bioadhesive microparticles absorption of aqueous media and swelling upon contact with one or more wet tissue surfaces generally refers to an increase in size by the dry bioadhesive microparticles.

As used herein, "biodegradable" when used to describe the dry bioadhesive microparticles refers the decomposition and/or subsequent removal of the implanted material in part or whole within the living animals by the endogenous enzymes and/or water inside the animals.

The present invention generally provides an adhesive material that is capable of forming instant, tough, and strong adhesion with diverse materials even in the presence of fluids. In particular, the adhesive material is capable of adhering to various tissue surfaces and adhering various tissue surfaces together even in the presence of fluids. Such fluids may include, but are not limited to water, saline, moisture, and physiological body fluids including blood, saliva, gastrointestinal fluid, mucus, and succus.

The adhesive material is fabricated of a hydrophobic oil matrix with bioadhesive microparticles dispersed therein, so as to provide a repel-crosslinking mechanism. Upon application of the adhesive material to a surface covered with a fluid and application of gentle pressure, the hydrophobic oil matrix repels the fluid to clean the surface and the bioadhesive microparticles subsequently form crosslinks with each other and with the underlying cleaned wet tissue surface. The adhesive material provides tough (i.e., interfacial toughness of at least about 100 J m$^{-2}$, and even as high as at least about 240 J m$^{-2}$) and strong (i.e., shear strength of at least about 30 kPa, and even as high as at least about 70 kPa, and tensile strength of at least about kPa and even as high as at least about 50 kPa) adhesion upon application of gentle pressure (a pressure of no greater than about 50 kPa, for example ranging from about 1 kPa to about 50 kPa) for a time period ranging from about 5 seconds to about 30 seconds on a broad range of fluid covered surfaces. As such, the present invention adhesive material is particularly useful in a variety of applications, including emergency trauma situations, wherein rapid and robust sealing/adhesion (e.g., hemostatic sealing of severely bleeding aorta) is necessary. The present invention adhesive material requires neither UV irradiation to form adhesion nor prolonged steady pressure application and, thus, overcomes the limitations of the existing adhesive materials.

Reference will now be made in detail to embodiments of the present invention, examples of which are illustrated in the accompanying drawings. Wherever possible, the same reference numbers are used in the drawings and the description to refer to the same or like parts.

According to one aspect, the present invention provides an adhesive material 1 comprising combination of: a hydrophobic matrix 2, particularly a hydrophobic oil matrix, and dry bioadhesive microparticles 3. The dry bioadhesive microparticles 3 are evenly dispersed within the hydrophobic matrix 2 such that the hydrophobic matrix 2 acts as a protective matrix (see FIG. 1A). Prior to use, one would preferably ensure that the adhesive material 1 is a homogenous mixture of the dry bioadhesive microparticles 3 dispersed within the hydrophobic matrix 2 by vigorously shaking stirring, or the like. As depicted in FIGS. 1A-C, when the adhesive material 1 is applied to a tissue surface 100 covered in fluid (in this case, blood-covered porcine skin tissue) and gentle pressure is applied (as depicted in FIG. 1E pressing by a gelatin-coated glass substrate), the hydrophobic matrix 2 protects the dry bioadhesive microparticles 3 from the body fluids and repels the body fluids thereby clearing the surface (FIG. 1B). This allows the dry bioadhesive microparticles 3 to contact one another and contact the wet tissue surface 100. As such, the present invention adhesive material 1 provides fluid resistance to achieve instant robust adhesion of tissues covered by fluids (e.g., water, saline, moisture, interstitial fluids, and body fluids such as blood, saliva, gastrointestinal fluid, mucus, and succus).

Figure 2D:
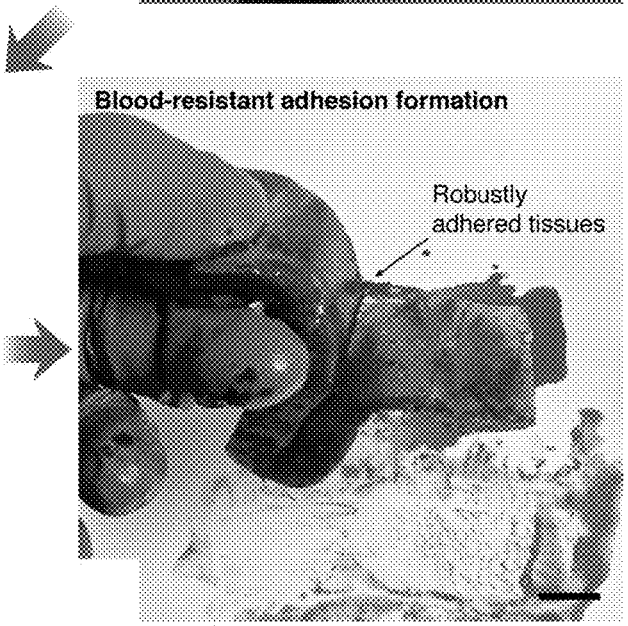

According to an embodiment of the invention, the adhesive material 1 is in the form of an injectable material comprising a hydrophobic matrix 2 with dry bioadhesive microparticles 3 dispersed therein (e.g., see FIGS. 1A, 3E, 4, 8B, 8D, 8F, 8H, 8J). Upon application of gentle pressure (e.g., 10 kPa), the hydrophobic matrix 2 repels the body fluids allowing the dry bioadhesive microparticles 3 to contact one another and to contact the cleaned wet tissue surface (e.g. see FIGS. 1B, 1E, 4). Subsequently, the dry bioadhesive microparticles 3 crosslink with each other and with the wet tissue surface 100 to form robust adhesion within about 5 seconds without the need for additional stimuli such as UV irradiation (e.g., see FIGS. 1C, 1F, 2). For example, as depicted in FIGS. 2A-D, two porcine heart tissues were covered with blood (FIG. 2A) and the present invention tissue adhesive was applied on the blood covered tissue (FIG. 2B), after which gentle pressure was applied for 5 seconds (FIG. 5C) resulting in robust adhesion formed between the two blood covered tissue surfaces (FIG. 2D).

According to one aspect, the dry bioadhesive microparticles 3 are formed from a dry bioadhesive material comprising a combination of: (i) one or more hydrophilic polymers or copolymers, (ii) one or more amine coupling groups, and (iii) one or more cross linkers.

According to embodiments of the present invention, the (i) hydrophilic polymers or copolymers are selected from any conventional hydrophilic polymers or copolymers that absorb water at a dry state. Such suitable hydrophilic polymers or copolymers include, but are not limited to, polyacrylic acid, polyacrylamide, polyvinyl alcohol, polyhydroxy ethyl methacrylate, polyethylene glycol, poly vinyl pyrrolidone, poly styrene sulfonate, polyurethane, casein, albumin, collagen, gelatin, chitosan, hyaluronic acid, alginate, oxidized alginate, pectin, cellulose, and oxidized cellulose, and combinations thereof. Because the present adhesive material can be used in a wide variety of biomedical applications, the polymers used in the present invention are preferably biocompatible (although for non-biomedical applications it would not be necessary to utilize only biocompatible polymer materials).

According to embodiments of the present invention, the (i) one or more hydrophobic polymers or copolymers are grafted with (ii) one or more amine coupling groups. Suitable amine coupling groups are selected from conventional amine coupling groups, including but not limited to, N-hydroxysuccinimide ester, N-hydroxysulfosuccinimide ester, aldehyde, imidoester, epoxide, isocyante, cathechol, and combinations thereof. Because the present adhesive material can be used in a wide variety of biomedical applications, the amine coupling groups used in the present invention are preferably biocompatible (although for non-biomedical applications it would not be necessary to utilize only biocompatible amine coupling groups). The amine coupling groups are configured such that the one or more hydrophilic polymers or copolymers can be grafted with the one or more amine-coupling groups, and such that the one or more amine coupling groups subsequently form covalent crosslinks with the surface on which the adhesive material is adhered.

According to embodiments of the present invention, the hydrophilic polymers or copolymers are preferably crosslinked with (iii) one or more crosslinkers are selected from conventional crosslinkers. Such crosslinkers include, but are not limited to, gelatin methacrylate, hyaluronic acid methacrylate, oxidized methacrylic alginate, polycaprolactone diacrylate, N,N'-bis(acryloyl) cystamine, N,N'-methylenebis (acrylamide), polyethylene glycol diacrylate, polyethylene glycol dimethacrylate, and combinations thereof. Because the present adhesive material can be used in a wide variety of biomedical applications, the crosslinkers used in the present invention are preferably biocompatible (although for non-biomedical applications it would not be necessary to utilize only biocompatible crosslinkers).

According to a preferred embodiment, the dry bioadhesive microparticles 3 are prepared by first fabricating the bioadhesive material fabricated of a combination of (1) one or more hydrophilic polymers or copolymers, (ii) one or more amine coupling groups, and (iii) one or more crosslinkers, and deionized water. According to an embodiment of the invention, suitable amounts of the various components used in preparing the bioadhesive material would range from (i) about 20 w/w % to about 55 w/w % of one or more hydrophilic polymers, (ii) about 0.5 w/w 10% to about 1.5 w/w % of one or more amine coupling groups, and (iii) and about 0.05 w/w % to about 0.15 w/w % of one or more crosslinkers, and deionized water for the remaining parts in its as-prepared (before drying) form.

According to an exemplary embodiment, the bioadhesive material comprises about 30 w/w % poly(acrylic acid), about 2 w/w % chitosan, about 1 w/w % PAAc-NHS ester, about 0.1 w/w % gelatin methacrylate, and deionized water for the remaining parts in its as-prepared (before drying) form.

Figure 3A:
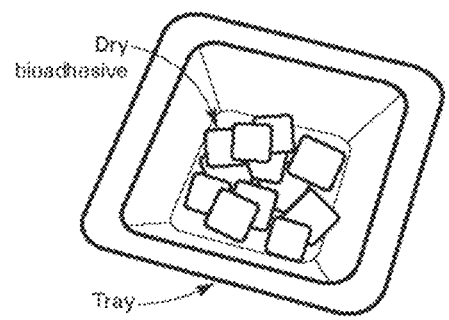
Figure 3B:
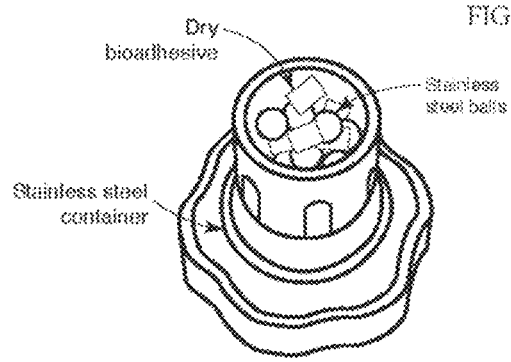
Figure 3C:
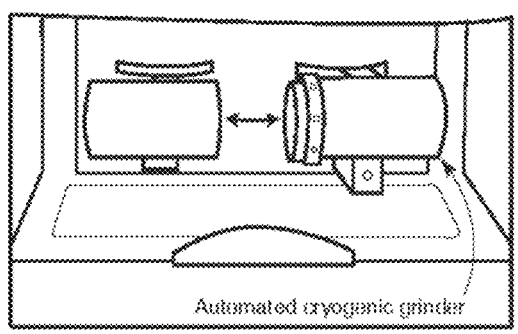
Figure 3D:
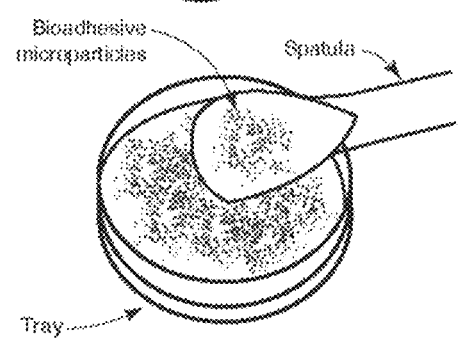
Figure 3E:
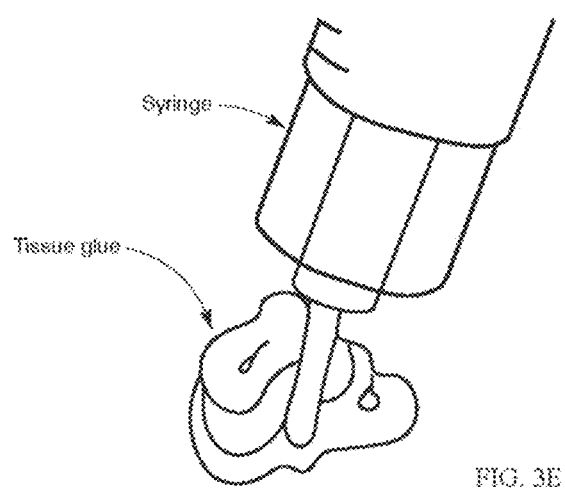

The as-prepared bioadhesive material is then dehydrated, and the dehydrated bioadhesive material is subjected to cryogenic grinding to produce dry bioadhesive microparticles 3 of a desired average particle size. For example as depicted in FIGS. 3A-E, the dry bioadhesive is first cut into small pieces (FIG. 3A), then the dry bioadhesive is added to a stainless steel container with stainless steel balls (FIG. 3B), then the dry bioadhesive is ground under cryogenic condition by using a cryogenic ball mill (FIG. 3C), to produce the dry bioadhesive microparticles 3 (FIG. 3D). The thus formed dry bioadhesive microparticles 3 are then mixed with a desired hydrophobic matrix 2 at a desired ratio to prepare the adhesive material 1, which is depicted as being injected through a syringe onto a blood covered porcine heart (FIG. 3E). When the adhesive material 1 is used as a tissue adhesive, the hydrophobic matrix 2 is a biocompatible matrix material. Suitable hydrophobic matrix 2 materials include, but are not limited to silicone oils, mineral oils, essential oils, perfluoropolyether oils, and/or lanolin oils.

According to an exemplary embodiment, the adhesive material 1 comprises dry bioadhesive microparticles fabricated of (i) poly(acrylic acid) grafted with N-hydroxysuccinimide ester (PAAc-co-NHS ester) crosslinked by biodegradable gelatin methacrylate and (ii) biodegradable chitosan, dispersed in a medical-grade silicone oil hydrophobic matrix.

Figure 7:
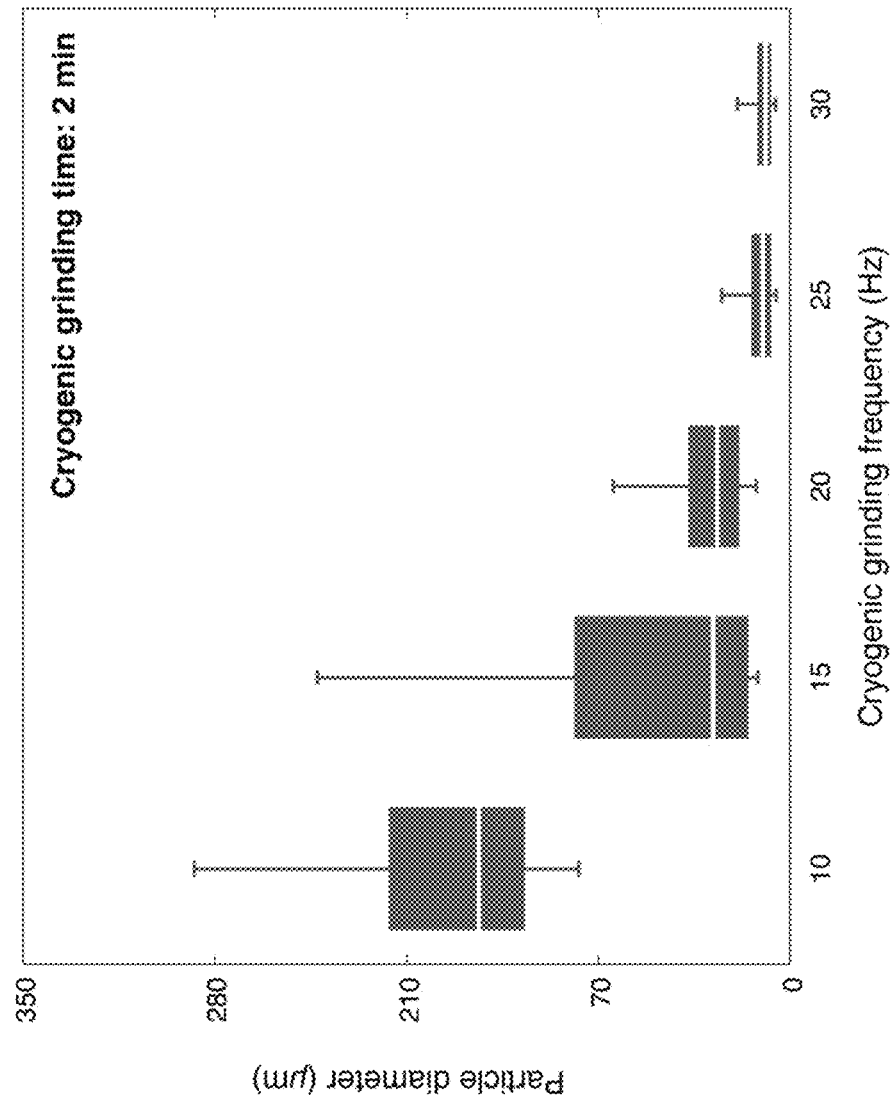
FIG. 7 graphically depict the size of dry bioadhesive microparticles under varying cryogenic grinding frequency, with the whiskers corresponding to the upper extreme and the lower extreme. The lines indicate the median and the error bars indicate the upper quartile and the lower quartile; N=3.

According to embodiments of the present invention, the average size of the dry bioadhesive microparticles 3 can be controlled by the cryogenic grinding conditions. In particular, as set forth in FIG. 7, the grinding time was fixed to 2 minutes and the grinding frequency was varied from 10 Hz to 30 Hz (particularly 10 Hz, 15 Hz, 20 Hz, 25 Hz, and 30 Hz). As demonstrated in FIG. 7, a higher grinding frequency resulted in a smaller average size of dry bioadhesive microparticles (~200 µm at 10 Hz and ~10 µm at 30 Hz). As such, a desired average size of the bioadhesive microparticles 3 can be achieved depending upon the adhesive material 1 use and specifications.

As depicted in FIGS. 8A-J, the resultant cryogenically ground bioadhesive microparticles 3 were used to fabricate adhesive materials 1 by adding these bioadhesive microparticles 3 to a hydrophobic matrix material 2 and the injectability of the resultant adhesive materials 1 was demonstrated by injection through a syringe. In particular, a SEM image of the dry bioadhesive microparticles 3 at 10 Hz cryogenic grinding frequency (FIG. 8A) and the corresponding adhesive material 1 pressured through a syringe with 2.5-mm diameter (FIG. 8B), a SEM image of the dry bioadhesive microparticles 3 at 15 Hz cryogenic grinding frequency (FIG. 8C) and the corresponding adhesive material 1 pressured through a nozzle with 1.2-mm diameter (FIG. 8D), a SEM image of the dry bioadhesive microparticles at 20 Hz cryogenic grinding frequency (FIG. 8E) and the corresponding adhesive material 1 pressured through a nozzle with 1.2-mm diameter (FIG. 8F), a SEM image of the dry bioadhesive microparticles at 25 Hz cryogenic grinding frequency (FIG. 8G) and the corresponding adhesive material 1 pressured through a nozzle with 1.2-mm diameter (FIG. 8H), and a SEM image of the dry bioadhesive microparticles at 30 Hz cryogenic grinding frequency (FIG. 8I) and the corresponding adhesive material 1 pressured through a nozzle with 1.2-mm diameter (FIG. 8J) are illustrated. For all of the adhesive materials 1, the cryogenic grinding time was 2 min for all cases and the same hydrophobic matrix material 2 was used for all adhesive materials 1.

Figure 9E:
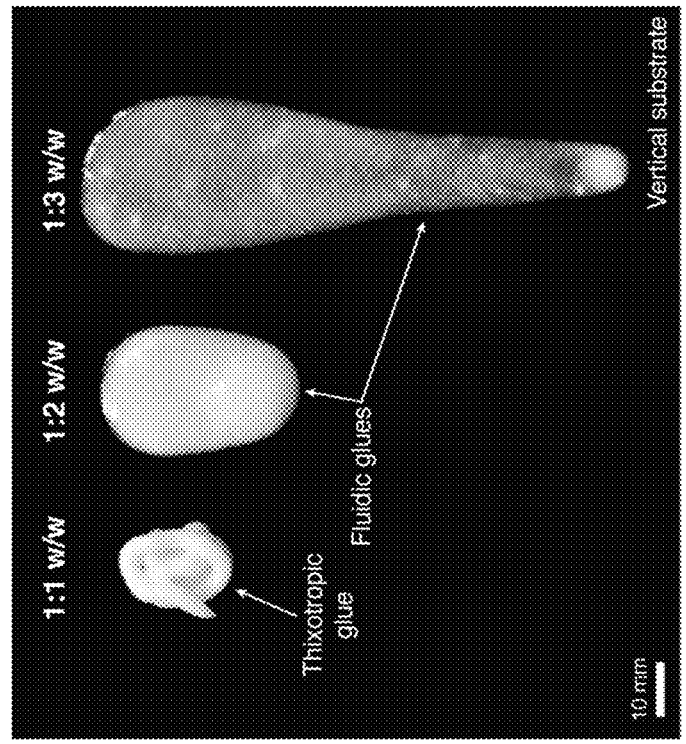
FIGS. 9A-E show photographs of the tissue adhesive with varying mixing ratio according to embodiments of the present invention together with injection on a vertical substrate to illustrate flowability, where mass ratio between the dry bioadhesive microparticles and the silicone oil matrix is 1:3 (9A), 1:2 (9B), 1:1 (9C), and 1:0.5 (9D).
Figure 9A:
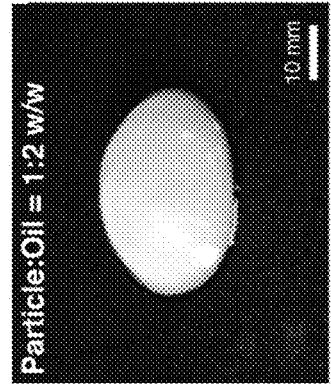
Figure 9B:
Figure 9C:
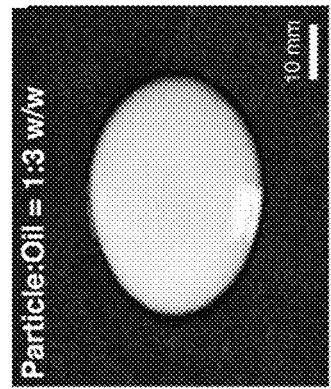
Figure 9D:
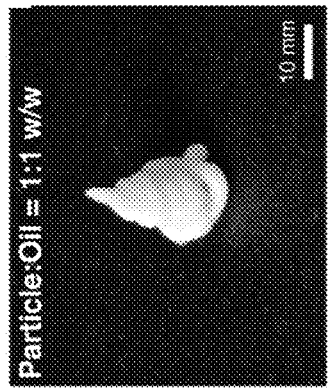

According to embodiments of the present invention, rheological properties (i.e., flow behavior, viscosity, shear yield stress) of the adhesive material 1 were tuned by controlling the mixing ratio between the dry bioadhesive microparticles 2 and the hydrophobic matrix 2. As demonstrated in FIGS. 8b, 8D, 8F, 8H, 8J and 9A-E, the adhesive material 1 ranged from viscous fluids to a stable thixotropic paste. In order to visualize flowability of the adhesive material 1, the adhesive materials 1 with varying mixing ratios were photographed, wherein mass ratio between the dry bioadhesive microparticles 3 and a hydrophobic silicone oil matrix 2 was set at 1:3 (FIG. 9A), 1:2 (FIG. 9B), 1:1 (FIG. 9C), and 1:0.5 (FIG. 9D). The adhesive materials 1 with mixing ratios 1:1, 1:2 and 1:3 were photographed in FIG. 9E as injected on a vertical substrate to further demonstrate flowability.

The dry bioadhesive microparticles 3 are formed and are dispersed within a hydrophobic matrix 2 so as to form instant strong adhesion on a desired surface and/or between themselves when used as described herein. For example, as schematically depicted in FIG. 4, the adhesive material 1 can be applied directly on the desired fluid covered surfaces (e.g., tissue surfaces covered by body fluids) without any other preparation or cleaning process (FIG. 4 steps 1-2). Upon application of gentle pressure, (FIG. 4, steps 3-4) the hydrophobic matrix repels and cleans the body fluids from the tissue surfaces (in this case, the adhesive material is disposed between two tissue surfaces covered in body fluids). Simultaneously, physical bond forming groups such as carboxylic acid groups in the bioadhesive microparticles form temporary crosslinks by intermolecular bonds (FIG. 4, step 5), followed by the formation of stable covalent crosslinking between amine-coupling groups such as NHS ester groups and the primary amine groups with themselves and with the cleaned wet tissue surfaces (FIG. 4, step 6). After adhering to/between the wet tissue surfaces, the swollen and crosslinked adhesive material forms a thin layer of hydrogel which provides robust adhesion between the tissues (FIG. 4, step 7).

Figure 5:
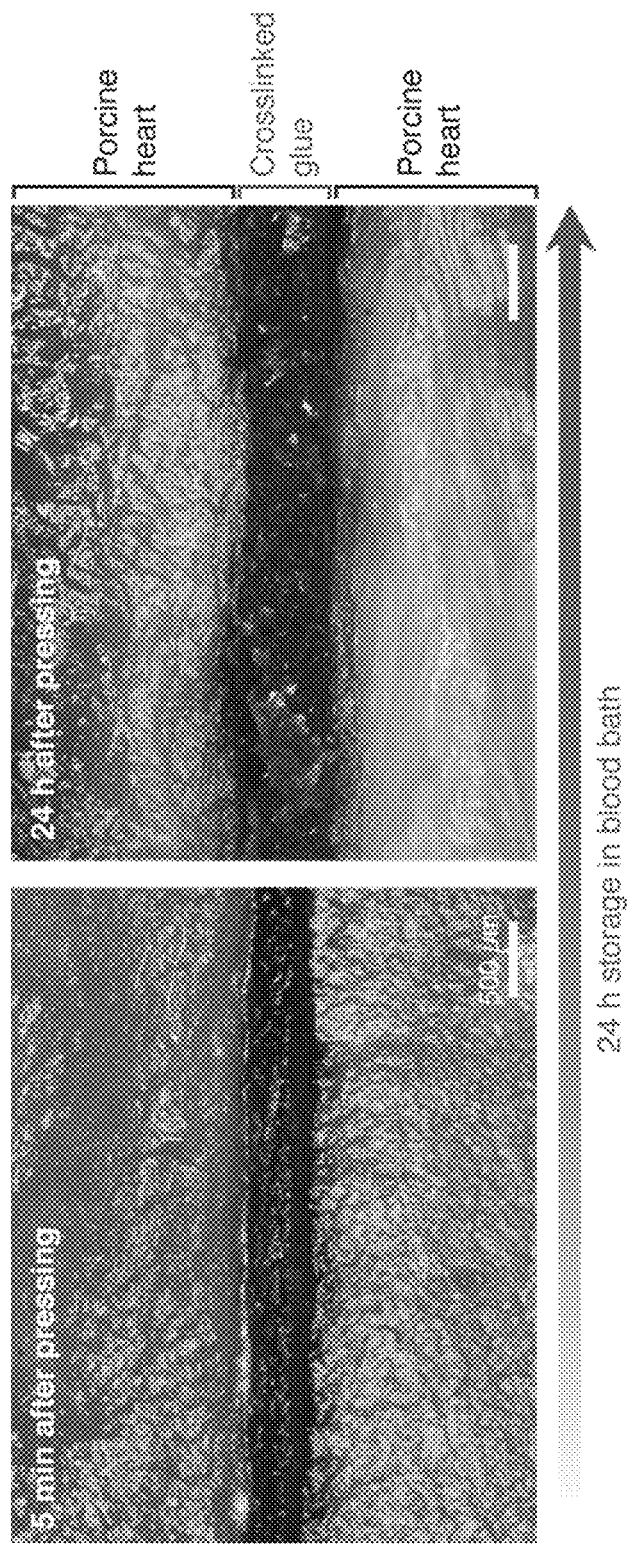
FIG. 5 show photographs of a cross-sectional view of two blood-covered porcine heart tissues adhered by the tissue adhesive material 5 min and 24 h after the application, according to an embodiment of the present invention.
Figure 6:
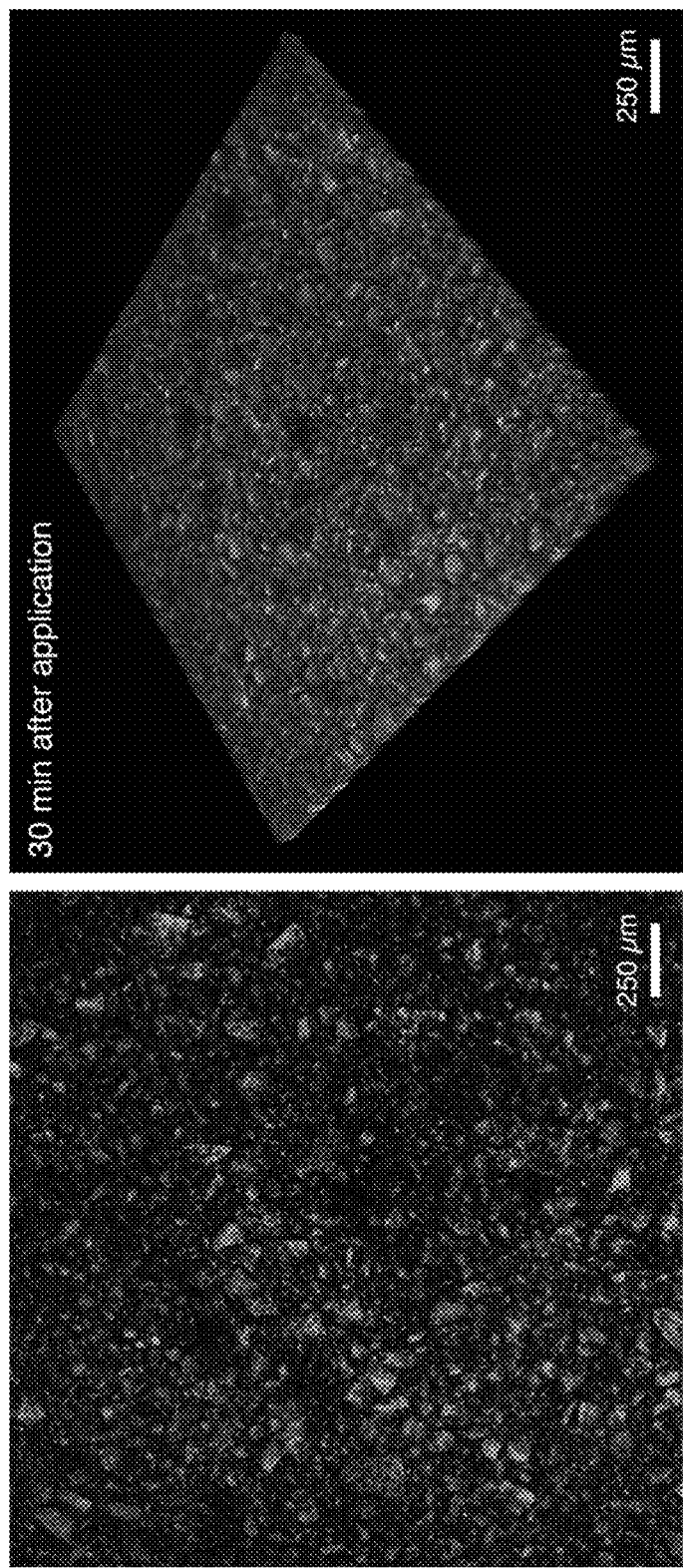
FIG. 6 show confocal microscope images of a swollen and crosslinked adhesion layer of the tissue adhesive between two gelatin hydrogels 30 min after the application, according to am embodiment of the present invention.

Photographs of cross-sectional views of two blood-covered porcine heart tissues adhered by the adhesive material 1 of the present invention are shown in FIG. 5, with the left photo showing the adhesion after 5 min and the right photo showing adhesion 24 h after the application (the sample is kept in a wet environment throughout the experiment). As depicted in FIG. 6, confocal microscope images show the swollen and crosslinked adhesion layer of the adhesive material between two gelatin hydrogels 30 min after application. In particular, as described herein, the adhesive material is in the form of dry bioadhesive microparticles that absorbs aqueous media from a wet biological tissue when placed into contact with the wet tissue surface, which causes the dry bioadhesive microparticles to swell. This absorption of aqueous media and swelling of the dry bioadhesive microparticles provides instant temporary crosslinking between the adhesive material and the wet surface, and further allows for fast subsequent covalent coupling or crosslinking between the adhesive material and the wet surface.

In order to demonstrate the structures and function of the adhesive material 1 components in tissue adhesion, pull-off tests were performed using the setup and procedure for pull-off tests illustrated in FIG. 10A, where the surface area of porcine heart tissues adhered was 1 cm 2. The pull-off force between porcine heart tissues adhered by the dry bioadhesive microparticles 3 without and with a hydrophobic silicone oil matrix was tested. The results of the pull-off tests performed in a phosphate buffered saline (PBS) bath show similarly high pull-off force (p=0.48) between the dry bioadhesive microparticles 3 without and with the silicone oil matrix 2 (FIG. 10B). These results indicate that the dry bioadhesive microparticles alone can provide instant strong adhesion between wet tissues in the absence of body fluids. The pull-off tests performed in a porcine blood bath, on the other hand, exhibit high pull-off force for the dry bioadhesive microparticles mixed with the silicone oil matrix, while the dry bioadhesive microparticles without the silicone oil matrix resulted in significantly lower pull-off forces (FIG. 10C).

To illustrate the roles of applied pressure and the property of the silicone oil matrix in adhesion to tissue surfaces, the pull-off force between porcine heart tissues adhered by the present invention adhesive material with varying applied pressure as well as viscosity of the silicone oil matrix was tested (FIG. 10E). As shown, as the applied pressure increased, the pull-off force first increased and then reached a plateau above a certain threshold of applied pressure (e.g., 10 kPa for silicone oil with 5 cSt kinematic viscosity). Moreover, the silicone oil with a higher viscosity showed a higher threshold of the applied pressure (e.g., 16 kPa for silicone oil with 100 cSt kinematic viscosity), agreeing with a granular suspension theory in the literature (E. Guazzelli, O. Pouliquen, Rheology of dense granular suspensions. *Journal of Fluid Mechanics* 852, (2018)).

Further, as depicted in FIG. 10D, the hydrophobic matrix's 2 role as a protective matrix for the dry bioadhesive microparticles 3 against body fluids on the tissue surface was demonstrated using the total surface energies of three configurations: i) Configuration 1 in which the dry bioadhesive microparticles are completely wetted by the silicone oil with a layer of body fluids facing below it (protected state, $E_1$), ii) Configuration 2 in which the dry bioadhesive microparticles are completely wetted by body fluids with a layer of the silicone oil facing below it (unprotected state, E 2), and iii) Configuration 2 in which the dry bioadhesive microparticles are completely wetted by the silicone oil without body fluids (repelled state, E 3). To ensure the energetically stable protection of the dry bioadhesive microparticles and the repelling of body fluids by the silicone oil matrix, one should satisfy $\Delta E_A = E_2 - E_1 > 0$ and $\Delta E_B = E_1 - E_3 > 0$ which can be expressed as:

$$R(\gamma_{oil/air} \cos \theta_{oil/ad} - \gamma_{bf/air} \cos \theta_{bf/ad}) + \gamma_{bf/air} \cos \theta_{bf/tissue} - \gamma_{oil/air} \cos \theta_{oil-/issue} > 0 \quad (1)$$

$$\gamma_{oil/bf} + \gamma_{oil/air} \cos \theta_{oil/tissue} - \gamma_{bf/air} \cos \theta_{bf/tissue} > 0 \quad (2)$$

where R is the roughness factor representing the ratio of the actual and projected surface areas of the dry bioadhesive microparticles, $\gamma_{A/B}$ represents the interfacial energy between A and B, and $\theta_{A/B}$ represents the contact angle of A on B (subscript "ad" represents bioadhesive microparticle; "bf" represents body fluid). Note that we take R as π for the dry bioadhesive microparticles in the adhesive material based on the first-order approximation of tightly placed spherical particles with the same diameter. By plugging the corresponding values in the Eqs. (1-2) (R=π, $\gamma_{oil/air}$=20.9 mN$^{m-1}$, $\gamma_{bf/air}$=72.0 mN m$^{-1}$, $\gamma_{oil/bf}$=40 mN m$^{-1}$, $\theta_{oil/ad}$=4.5°, $\theta_{bf/ad}$=96°, $\theta_{oil/tissue}$=4.2°, $\theta_{bf/tissue}$=84°), it is evident that the adhesive material satisfies these inequalities. Hence, the silicone oil matrix protects the dry bioadhesive microparticles against body fluids and repel the body fluid from the tissue surface, demonstrating the present invention adhesive material design and mechanism.

Figure 11:
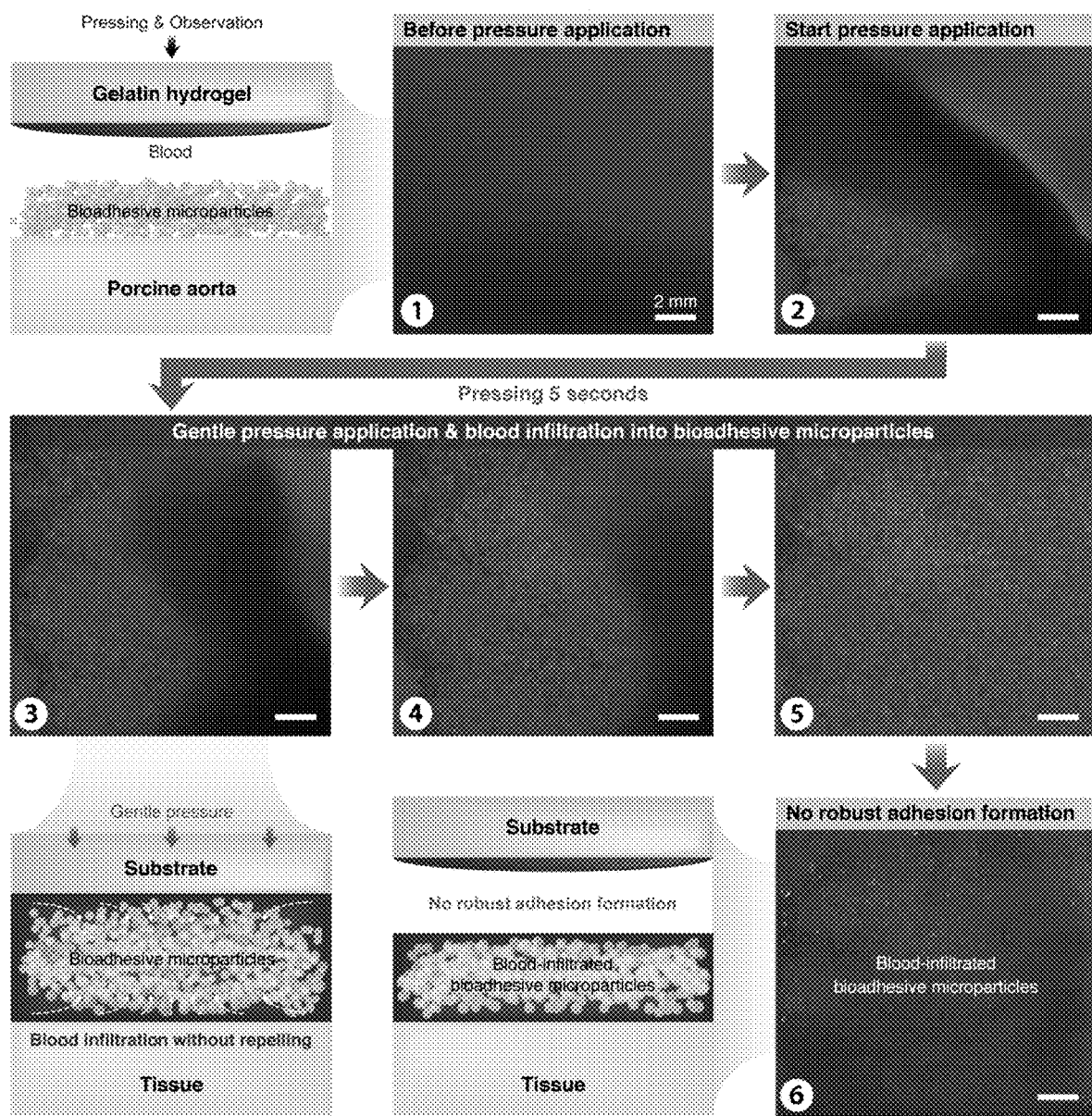
FIG. 11 illustrates use of dry bioadhesive microparticles without a hydrophobic oil matrix, wherein infiltrated blood swells and inactivates the bioadhesive microparticles such that no adhesion formed between the gelatin hydrogel and the porcine aorta.

Thus, in the absence of a protective hydrophobic matrix 2, body fluids can readily infiltrate into and interact with the dry bioadhesive microparticles 3, preventing the formation of robust adhesion among the microparticles and/or with the tissue surface. These results indicate that the hydrophobic matrix 2 of the present invention adhesive material 1 effectively protects and preserves the dry bioadhesive microparticles 3 in the presence of body fluids. In particular, as illustrated in in FIG. 11, (i) a blood-covered gelatin hydrogel was placed on top of a porcine aorta covered with a layer of dry bioadhesive microparticles without a hydrophobic matrix, then (ii) the blood-covered gelatin hydrogel was pressed on the tissue, (iii) blood started to infiltrate into the bioadhesive microparticles, (iv-v) infiltrated blood swelled and inactivated the bioadhesive microparticles, and (vi) no adhesion was formed by the dry bioadhesive microparticles between the gelatin hydrogel and the porcine aorta.

Figure 12:
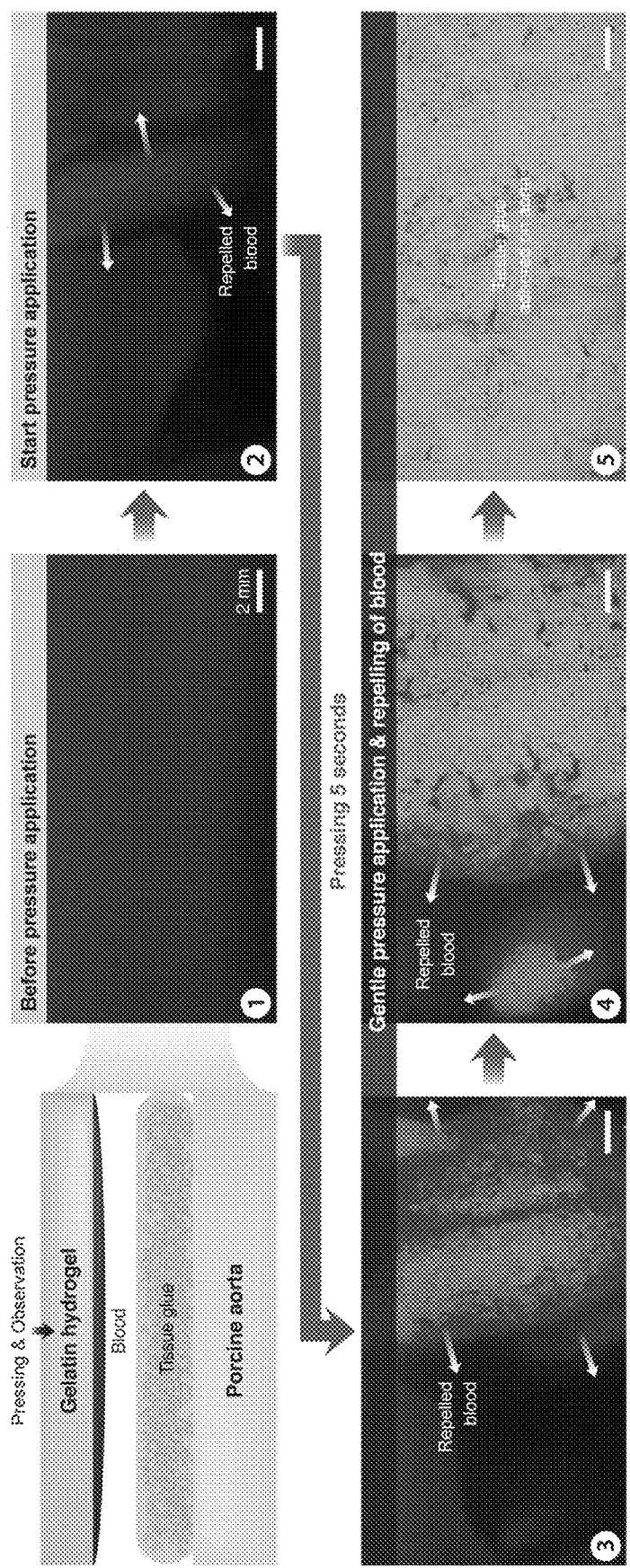
FIG. 12 illustrates the blood repelling process by the tissue adhesive according to an embodiment of the present invention, wherein blood on the tissue surface is repelled and cleaned by the tissue adhesive, and the tissue adhesive forms robust adhesion between the gelatin hydrogel and the porcine aorta.

On the other hand, the blood repelling process by the present invention adhesive material containing dry bioadhesive microparticles 3 dispersed within a hydrophobic matrix 2 is demonstrated in FIG. 12. As shown, (i) a blood-covered gelatin hydrogel was placed on top of a porcine aorta covered with a layer of the present invention adhesive material, then (ii) the blood-covered gelatin hydrogel was pressed on the tissue, (iii) blood started to be repelled by the adhesive material, (iv) blood on the tissue surface was cleaned from the tissue surface by the adhesive material, and (v) the adhesive material formed robust adhesion between the gelatin hydrogel and the cleaned porcine aorta. In particular, upon application of gentle pressure, the dry bioadhesive microparticles 3 in the adhesive material 1 become densely compacted and form a non-flowable jammed adhesive layer. During this compaction process, the hydrophobic matrix 2 is pushed out of the adhesive material 1, repelling and cleaning body fluids from the tissue surface (FIG. 12). Thus, the applied pressure and the hydrophobic property of the silicone oil matrix allows for the adhesion formation of the adhesive material by the bioadhesive microparticles 3.

To further evaluate the adhesion performance of the adhesive material 1, three different types of mechanical tests were performed to measure (i) interfacial toughness using the testing setup based on the standard 180-peel test (ASTM F2256) (FIG. 13A), (i) shear strength using the testing setup based on the standard lap-shear test (ASTM F2255)(FIG. 13B), and tensile strength using the testing setup based on the standard tensile test (ASTM F2258) (FIG. 13C). Adhesion performance of the adhesive material 1 was then graphically depicted by plotting interfacial toughness vs. pressing time for adhered blood-covered porcine skin tissues (FIG. 14A), and by plotting interfacial toughness vs. storage time for adhered blood-covered porcine skin tissues (FIG. 14B). The present invention adhesive material 1 was demonstrated to form robust adhesion, with interfacial toughness over 240 J m$^{-2}$ between blood-covered porcine skin tissues upon contact and gentle pressure (10 kPa) application for less than 5 s, demonstrating the rapid body fluid resistant adhesion capability (FIG. 14A). The tissues adhered by the adhesive material 1 also showed no significant deterioration in the measured interfacial toughness (p=0.78) over 48 h storage after the initial pressing (FIG. 14B). Further, a comparison of adhesion performances between the present invention adhesive material 1 and various commercially-available tissue adhesives and glues on blood-covered porcine skin tissues (FIG. 14C) shows that the present invention adhesive material 1 possesses superior adhesion performance compared to existing commercially-available tissue adhesives and glues, including gelatin-based hemostatic sealants (e.g., Surgiflo®), fibrin-based hemostatic sealants (e.g., Tisseel, TachoSil®), albumin-based adhesives (e.g., BioGlue), PEG-based adhesives (e.g., Coseal), and cyanoacrylate adhesives (Histoacryl®). As shown in FIG. 14C, these commercially-available tissue adhesives and glues exhibit relatively slow adhesion formation (longer than 1 min) and limited adhesion performance on blood-covered porcine skin tissues (interfacial toughness lower than 30 J m$^{-2}$ and shear/tensile strength lower than 20 kPa). In contrast, the present invention adhesive material 1 demonstrates robust adhesion with interfacial toughness over 240 J m$^{-2}$, shear strength over 70 kPa, and tensile strength over 50 kPa in less than 5 s, significantly outperforming the commercially-available tissue adhesives and glues.

Figure 15A:
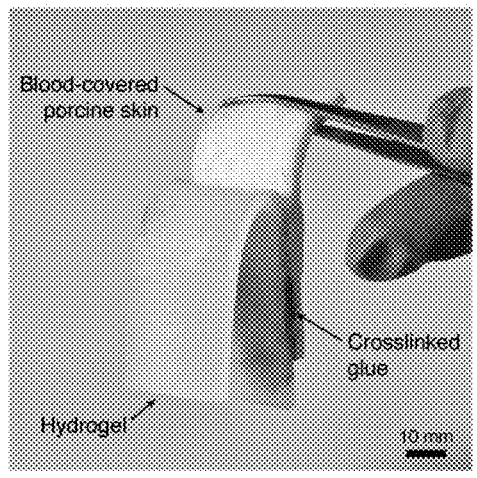
FIGS. 15A-B illustrate photographically the adhesion of a hydrogel and a blood-covered porcine skin by the tissue adhesive according to an embodiment of the present invention (FIG. 15A), and graphically the interfacial toughness, shear strength, and tensile strength between the hydrogel and blood-covered porcine skin adhered by the tissue adhesive (FIG. 15B). All samples were kept in wet environment before the mechanical tests. Error bars indicate SD; N=4.
Figure 15B:
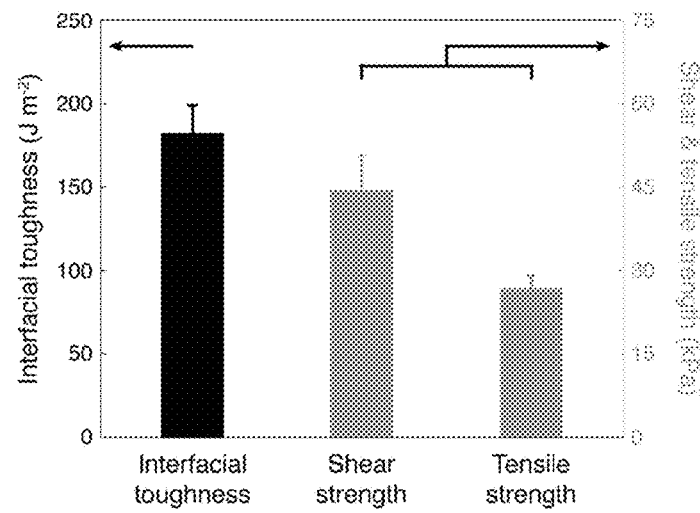

As further demonstrated in FIGS. 14D-E and 15, the present invention adhesive material is applicable for a broad range of body fluid covered tissues and hydrogels to form robust adhesion with high interfacial toughness (over 240 J m$^{-2}$ for skin, 150 J m$^{-2}$ for aorta, 140 J m$^{-2}$ for heart, 330 J m$^{-2}$ for muscle, and 170 J m$^{-2}$ for hydrogel covered with blood; over 120 J m$^{-2}$ for stomach and 100 J m$^{-2}$ for small intestine covered with mucus and gastric juice), shear and tensile strength (over 70 kPa for skin, 55 kPa for aorta, 45 kPa for heart, 50 kPa for muscle, and kPa for hydrogel covered with blood; over 30 kPa for stomach and 35 kPa for small intestine covered with mucus and gastric juice) in less than 5 sec.

The unique capability of the adhesive material 1 forming instant strong adhesion on tissues and organs covered by body fluids without the need for additional apparatus (e.g., UV) or without requiring that the surface first be cleaned of fluids prior to application of the adhesive material 1 would provide benefits for various clinical and biomedical applications. In order to explore potential applications of the adhesive material, the hemostatic sealing of ex vivo porcine aorta and in vivo rat heart models was studied using the adhesive material 1. As demonstrated in FIG. 16A, the adhesive material 1, combined with a commercially-available oxidized cellulose backing (Surgicel®, 2.5 cm×2.5 cm size) formed a robust hemostatic seal of a bleeding porcine aorta (3 mm hole; blood flow pressure at 150 mmHg) in less than 5 sec. The aorta sealed by the adhesive material 1 maintained adhesion under continuous blood flow and withstood a hyper-physiological pressure (250 mmHg) without leakage for 6 hours after the initial pressing of the adhesive material 1. Furthermore, blood from the bleeding porcine aorta was collected and filtered with a mesh (100-m mesh size) after the test (closed-loop flow for 6 hours). As depicted in FIG. 17 no bioadhesive microparticles were observed on the mesh, demonstrating the robustness of a hemostatic seal formed by the adhesive material 1 against a potential risk of embolization. To quantitatively evaluate the strength of hemostatic seals formed using the adhesive material 1, the burst pressure of the adhesive material 1 was measured by using porcine aorta tissues (ASTM F2392-04) (FIG. 16C). The adhesive material 1 demonstrated high burst pressure over 350 mmHg, significantly exceeding the normal systolic arterial blood pressure in human (~120 mmHg) and the performance of sutures and commercially-available hemostatic sealants (e.g., Surgiflo® and Tisseel).

It is noted that the oxidized cellulose backing material was introduced in this example to provide a non-tissue-adhesive cover for the injected adhesive material 1. In this example, the adhesive material 1 was provided at the target tissue site in the form of injectable paste-like or glue-like material, and the backing was subsequently placed on top of the deposited adhesive material 1 to facilitate in pressing it onto the target biological tissue. Similarly, backing materials may also be used for other adhesive material 1 deposition methods, such as painting or otherwise spreading the adhesive material 1 onto the tissue site. Various other backing material compositions can suitably be used in similar manner. Suitable backing material compositions include oxidized cellulose, silicone elastomer, polyurethane, hydrogel, any other biocompatible materials that do not adhere to wet tissue, and combinations thereof. In embodiments wherein the adhesive material 1 is placed between two surfaces (e.g. two tissue surfaces) and sandwiched therebetween to adhere the surfaces together, a backing material would not be necessary.

The adhesive material, thus, provides unique capabilities of forming instant strong adhesion on surfaces, such as tissues and organs, covered by fluids without the need for pre-cleaning of the surface, the use of additional apparatus (e.g., UV), and/or prolonged steady pressure application to form adhesion. As such, the adhesive material can be beneficial for use in various clinical and biomedical applications. The adhesive material's ability to quickly, precisely, and robustly adhere to surfaces covered by fluids can further address a need in treating traumatic, life-threatening injuries of tissues and organs on site, which are highly time-sensitive and complex in nature. The unique capabilities provided by the adhesive material address a set of long-lasting challenges in existing tissue adhesives and may offer new opportunities for future developments in tissue engineering, drug delivery, and bio-integrated devices. The new repel-crosslinking mechanism for wet adhesion may further inspire the design of future adhesives in wet and underwater environments.

EXPERIMENTAL DATA

Materials

All chemicals were obtained from Sigma-Aldrich unless otherwise mentioned and used without further purification. For preparation of dry bioadhesive, acrylic acid, gelatin methacrylate (gelMA; type A bloom 90-100 from porcine skin with 60% substitution), acrylic acid N-hydroxysuccinimide ester (AAc-NHS ester), α-ketoglutaric acid, and chitosan (75-85% deacetylated) were used. For matrix of dry bioadhesive microparticles, silicone oils with different viscosity (5 cSt and 100 cSt) were used. For visualization of the adhesive material, FITC-chitosan (KITO-8, PolySciTech) was used for confocal microscope images. For preparation of hydrogels, acrylamide, gelatin (type A bloom 300 from porcine skin), gelMA, and Irgacure 2959 were used. Porcine blood was purchased from Lampire Biological Laboratories, Inc. All porcine tissues for ex vivo experiments were purchased from a research-grade porcine tissue vendor (Sierra Medical Inc.).

Methods

Preparation of the body fluid resistant adhesive material. To prepare a bioadhesive, w/w % acrylic acid, 2 w/w % chitosan, 1 w/w % AAc-NHS ester, 0.1 w/w % gelMA, and 0.5 w/w % α-ketoglutaric acid were dissolved in deionized water. The mixture was then filtered with 0.4 μm sterile syringe filters and poured on a glass mold with 500-μm spacers. The bioadhesive was cured in a UV chamber (284 nm, 10 W power) for 60 min and completely dried under nitrogen flow for 24 h. The dry bioadhesive was sealed in plastic bags and stored in −20° C. before use. To aid visualization of the adhesive material for confocal microscope images, 0.2 w/w % FITC-chitosan was further added into the precursor solution before curing.

To prepare dry bioadhesive microparticles, the dry bioadhesive was cut into small pieces and added into a container of a cryogenic grinder (CryoMill, Retsch), followed by a cryogenic grinding process (30 Hz frequency for 2 min). The adhesive material was prepared by thoroughly mixing the dry bioadhesive microparticles and silicone oil matrix. The prepared adhesive material was sealed in plastic bags with desiccant (silica gel packets) and stored in −20° C. before use. Unless otherwise specified, the silicone oil with viscosity of 5 cSt and the 1:1 mass ratio (equivalent to volume fraction=0.4) between the dry bioadhesive microparticles and the silicone oil were used.

Mechanical tests. For tissue samples stored more than 10 min before mechanical tests, the samples were covered with a large amount of 0.01 w/v % sodium azide solution (in PBS) spray and sealed in plastic bags to prevent degradation and dehydration of the tissues. Unless otherwise indicated, all tissues and hydrogels were adhered by the adhesive material after covering with body fluids (blood or gastric juice) followed by 5 sec pressing (with 10 kPa pressure applied by either mechanical testing machine or equivalent weight). Unless otherwise indicated, all mechanical tests on adhesion samples were performed 6 hours after initial pressing to ensure equilibrium swelling of the adhered adhesive material in wet physiological environments. The application of commercially-available tissue adhesives and glues followed the provided manual for each product.

For pull-off tests, porcine heart tissues were cut with a surface area of 1 cm 2 and thickness of 5 mm. On one side, the porcine heart tissue was adhered to a glass container filled with a PBS or porcine blood bath by using a cyanoacrylate glue (Krazy Glue™). On another side, the porcine heart tissue was adhered to an aluminum fixture by using a cyanoacrylate glue and the surface of the tissue was covered by the dry bioadhesive microparticles without or with varying viscosity_silicone oil matrices (5 cSt or 100 cSt). The adhesive-covered porcine heart tissue was pressed against the tissue submerged in the bath at varying pressure by using a mechanical testing machine (2.5 kN load-cell, Zwick/Roell Z2.5) for 5 sec. The adhered tissues were then pulled by lifting the aluminum fixture and the maximum tensile force was measured as the pull-off force.

To measure interfacial toughness, the adhered samples with 2.5 cm in width were prepared and tested by the standard 180-degree peel test (ASTM F2256) with the mechanical testing machine. All tests were conducted with a constant peeling speed of 50 mm min$^{-1}$. The measured force reached a plateau as the peeling process entered the steady-state. Interfacial toughness was determined by dividing two times of the plateau force (for 180-degree peel test) with the width of the tissue sample (FIG. 13A). Poly(methyl methacrylate) film (50 μm thickness, Goodfellow) was applied by using a cyanoacrylate glue as a stiff backings for the tissues and hydrogels.

To measure shear strength, the adhered samples with an adhesion area of 2.5 cm in width and 1 cm in length were prepared and tested by the standard lap-shear test (ASTM F2255) with the mechanical testing machine (FIG. 13B). All tests were conducted with a constant tensile speed of 50 mm min$^{-1}$. Shear strength was determined by dividing the maximum force by the adhesion area. Poly(methyl methacrylate) film was applied using a cyanoacrylate glue as a stiff backings for the tissues and hydrogels.

To measure tensile strength, the adhered samples with adhesion area of 2.5 cm in width and 2.5 cm in length were prepared and tested by the standard tensile test (ASTM F2258) with the mechanical testing machine (FIG. 13C). All tests were conducted with a constant tensile speed of 50 mm min$^{-1}$. Tensile strength was determined by dividing the maximum force with the adhesion area. Aluminum fixtures were applied by using a cyanoacrylate glue to provide grips for the tensile tests.

Preparation of hydrogels. To prepare hydrogels for adhesion tests, 20 w/w % acrylamide, 10 w/w % gelatin, 0.2 w/w % gelMA, and 0.2 w/w % Irgacure 2959 were dissolved in deionized water. The mixture was then filtered with 0.4 μm sterile syringe filters and poured on a glass mold with 3-mm spacers. The hydrogels were cured in a UV chamber (284 nm, 10 W power) for 60 min.

Microscope imaging. Scanning electron microscope (SEM) images of the cryogenically ground dry bioadhesive microparticles were taken by using a SEM facility (JSM-6010LA, JEOL) with 5 nm gold sputtering to enhance image contrasts. Confocal microscope images of the adhesive material were obtained by an upright confocal microscope (SP8, Leica) with 490 nm excitation wavelength for FITC.

Contact angle measurement. The dry bioadhesive or a porcine skin tissue were bonded on a glass substrate and the contact angle of silicone oil and porcine blood was measured by using a contact angle apparatus (Rame-Hart). The contact angle measurements were conducted at room temperature (23-26° C.) with relative humidity of 35%.

Ex vivo tests. All ex vivo experiments were reviewed and approved by the Committee on Animal Care at the Massachusetts Institute of Technology. For hemostatic sealing of a bleeding aorta, a porcine aorta was connected with a porcine blood bath and a pump via silicone tubes to generate closed-loop blood flow at 150 mmHg pressure (FIG. 16A). A 3-mm diameter hole was made to the porcine aorta by a biopsy punch (Dynarex). To form hemostatic seal, 1 mL of the adhesive material was injected on a commercially-available degradable surgical gauze (Surgicel®, Ethicon) with area of 2.5 cm in width and 2.5 cm in length, and then gently pressed onto the punctured hole for 5 sec. The sealed porcine aorta was kept for 6 hours at room temperature with continuous blood flow to monitor the hemostatic sealing made by the adhesive material. 0.01 w/v % sodium azide solution (in PBS) was sprayed on the porcine aorta to avoid tissue dehydration and degradation. After the test, the blood bath was filtered by using a 100 μm mesh to check the presence of free-floating bioadhesive microparticles in the blood.

Figure 16B:
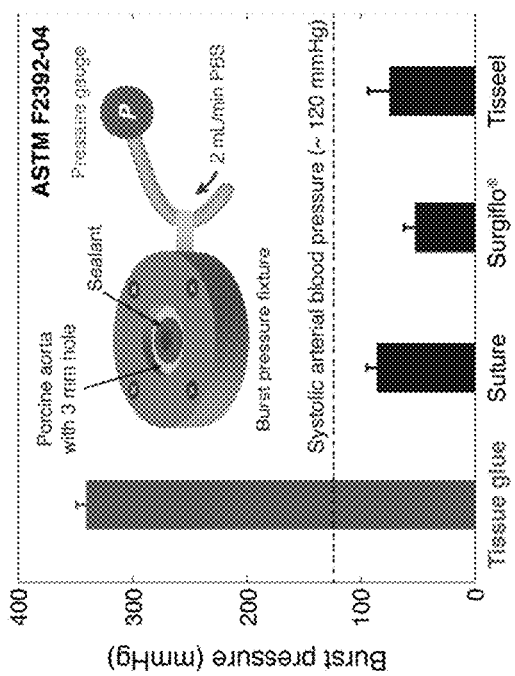
Figure 16A:
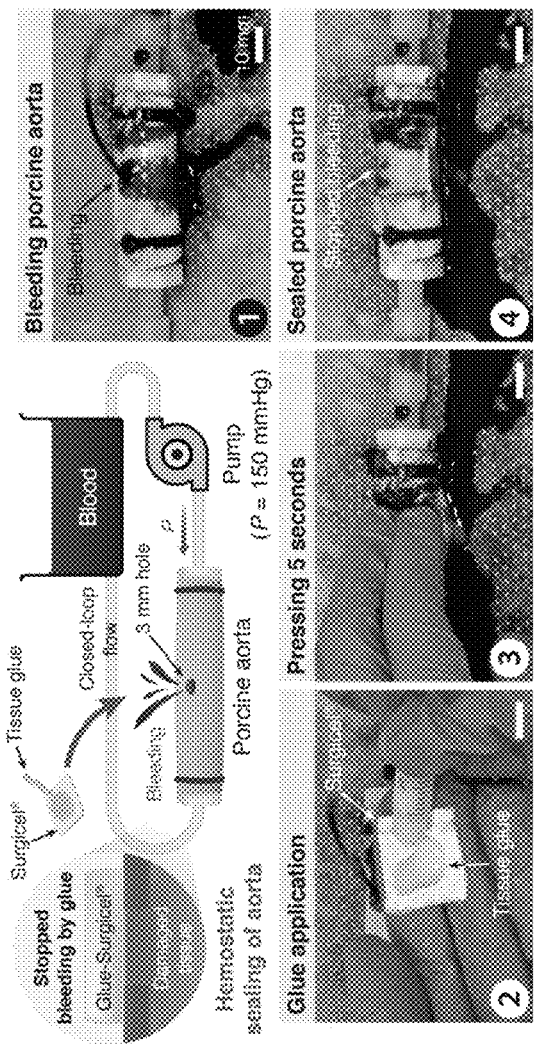
Figure 17:
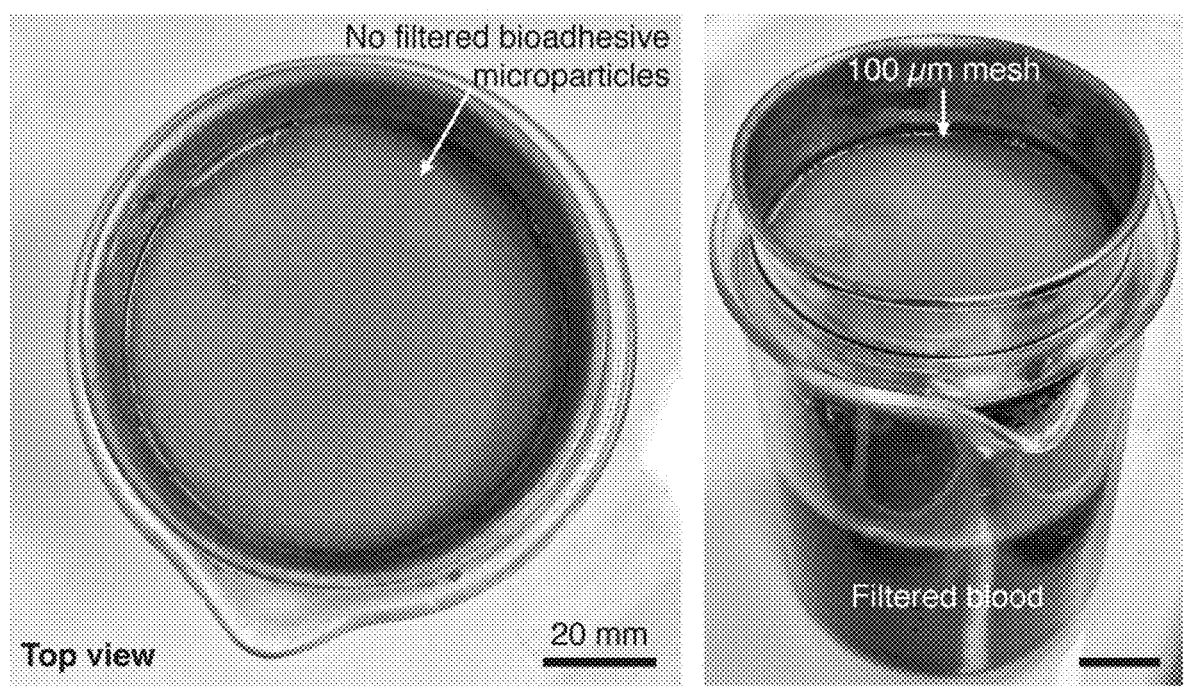
FIG. 17 photographically illustrates a porcine blood bath filtered with a 100 μm mesh after 6 hours continuous flow through an ex vivo porcine aorta sealed with a tissue adhesive according to an embodiment of the present invention, where no filtered bioadhesive microparticles are observed on the mesh.

To measure burst pressure, a porcine aorta with area of 2.5 cm in width and 2.5 cm in length was prepared and tested by the standard burst pressure test (ASTM F2392-04) (FIG. 16B). A 3-mm hole was introduced to the porcine aorta by using a biopsy punch (Dynarex). The punctured porcine aorta was then covered with porcine blood and sealed by using various adhesives (the adhesive material with Surgicel® backing, suture (Ethicon 4-0 vicryl), Surgiflo®, and Tisseel). 30 min after the sealing, pressure was applied to the sealed porcine aorta by pumping PBS using a syringe pump at a flow rate of 2 ml/min. The maximum pressure was recorded as the burst pressure by using a pressure gauge (Omega).

Biocompatibility and Biodegradability

Figure 18A:
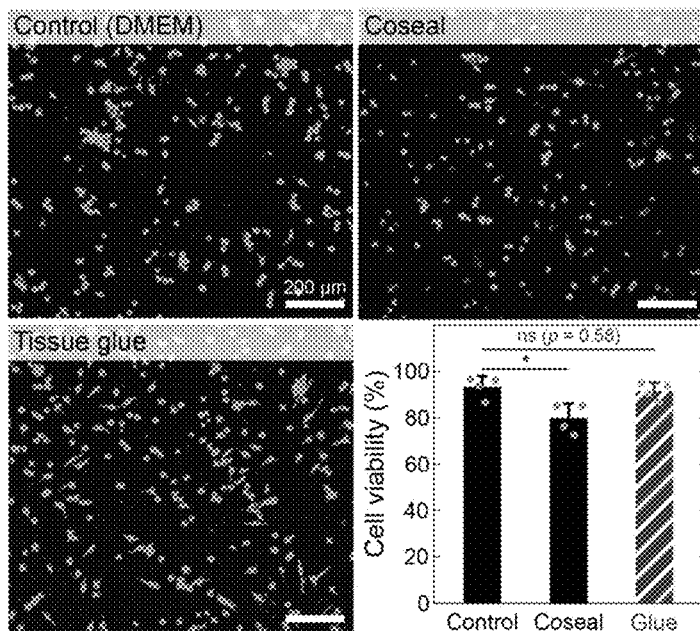
Figure 18B:
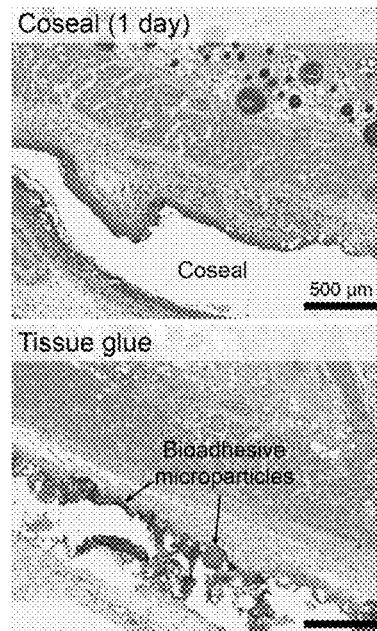
Figure 18C:
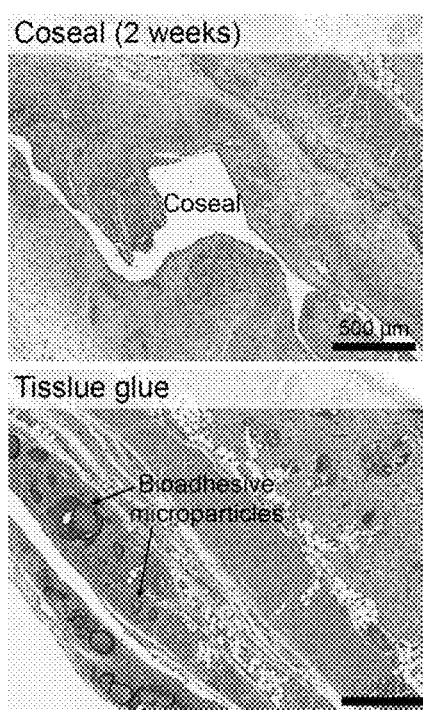
Figure 18D:
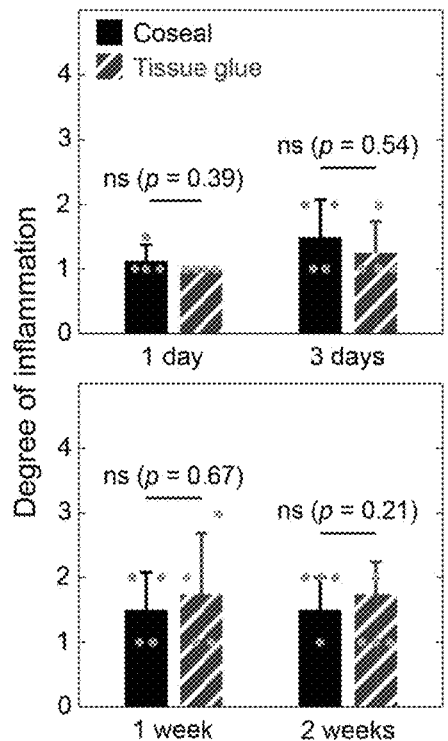
Figure 20B:
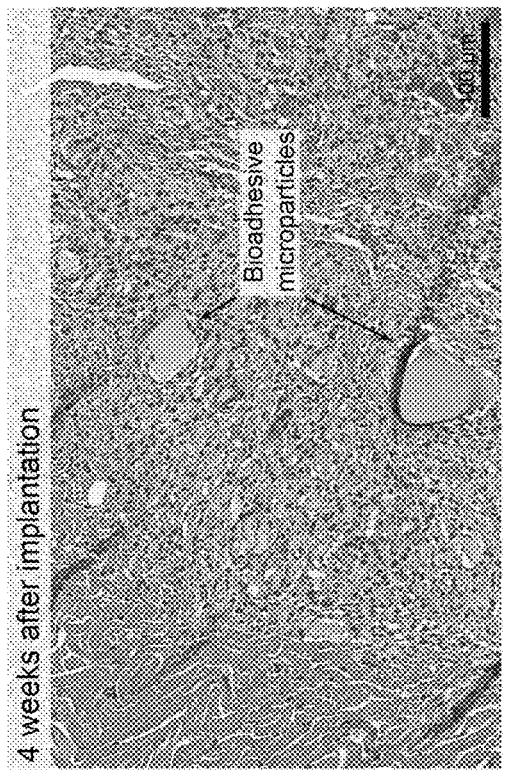
FIGS. 20A-D illustrate in vivo degradation of the present invention tissue adhesive, where
Figure 20D:
Figure 20A:
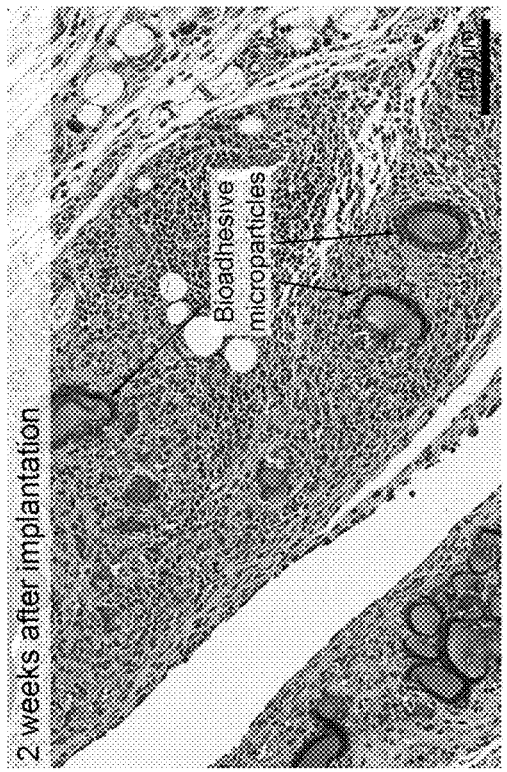
Figure 20C:
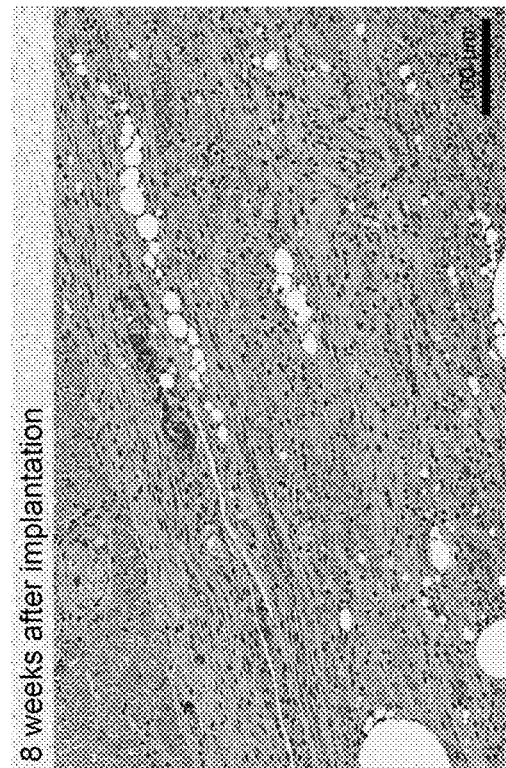

To evaluate biocompatibility and biodegradability of the tissue glue, in vitro and in vivo characterizations were performed based on rat models (FIGS. 18A-L). A cell culture media (DMEM) conditioned with the tissue glue exhibited comparable in vitro cytotoxicity of rat cardiomyocytes to a control (pristine DMEM) after 24-hour culture (FIG. 18A). In vivo biocompatibility of the tissue glue was e valuated based on dorsal subcutaneous implantation in rat models for various time points from 1 day to 2 weeks (FIGS. 18B-C and FIGS. 19A-B). Histological assessment by a blinded pathologist demonstrated that the tissue glue elicited very mild to mild inflammation comparable to a commercially-available U.S. Food and Drug Administration (FDA)-approved tissue adhesive Coseal at all time points ($p=0.39$ for 1 day, $p=0.54$ for 3 days, $p=0.67$ for 1 week, $p=0.21$ for 2 weeks, FIG. 18D). To further investigate in vivo biocompatibility of the tissue glue, immunofluorescence staining of various markers for fibroblast ($\alpha$SMA), type 1 collagen (Collagen I), T-cell (CD3), and macrophage (CD68) related to inflammatory and foreign body responses were performed (FIGS. 18E-H and FIGS. 19C-F). The normalized immunofluorescence intensity analysis demonstrated that the tissue glue induced no significant difference in the expression of $\alpha$SMA, Collagen I, CD3, and CD68 compared to that of Coseal for all time points (FIG. 18I-L). Notably, the tissue glue exhibited gradual biodegradation via resorption by macrophages over a longer period of implantation (FIG. 20A-C), and the rate of biodegradation can be accelerated by using faster degrading materials such as gelatin to replace chitosan in the bioadhesive microparticles (FIG. 20D).

Method for Biocompatibility and Biodegradability Evaluations

In vitro biocompatibility evaluation. In vitro biocompatibility tests were conducted by using the tissue glue-conditioned media for cell culture. To prepare the tissue glue-conditioned or Coseal-conditioned media, 0.5 ml of the tissue glue or Coseal were incubated in 10 mL DMEM supplemented with 10 v/v % fetal bovine serum (FBS) and 100 U ml-1 penicillin—streptomycin at 37° C. for 24 h. The supplemented DMEM without incubating the tissue glue was used as a control. Rat embryonic cardiomyocytes (H9c2 (2-1), ATCC) were plated in confocal dish (20-mm diameter) at a density of $0.5 \times 10^5$ cells (n=4 per each group). The cells were then treated with the tissue glue-conditioned media and incubated at 37° C. for 24 h in 5% CO2. The cell viability was determined by a LIVE/DEAD viability/cytotoxicity kit for mammalian cells (Thermo Fisher Scientific). A laser confocal microscope (SP 8, Leica) was used to image live cells with excitation/emission at 495 nm/515 nm, and dead cells at 495 nm/635 nm, respectively. The cell viability was calculated by counting the number of live (green fluorescence) and dead (red fluorescence) cells by using ImageJ (version 2.1.0).

In vivo biocompatibility and biodegradability evaluation. All animal surgeries were reviewed and approved by the Committee on Animal Care at the Massachusetts Institute of Technology. Female Sprague Dawley rats (225-250 g, Charles River Laboratories) were used for all in vivo studies. Prior to implantation, the tissue glue was prepared using aseptic techniques and were further sterilized for 3 h under UV light. For implantation in the dorsal subcutaneous space, rats were anaesthetized using isoflurane (1-2% isoflurane in oxygen) in an anesthetizing chamber. Anesthesia was maintained using a nose cone. Back hair was removed and the animals were placed over a heating pad for the duration of the surgery. The subcutaneous space was accessed by a 1-2 cm skin incision per implant in the center of the animal's back. To create space for implant placement, blunt dissection was performed from the incision towards the animal shoulder blades. Either 0.5 ml of the tissue glue (n=4 for each endpoint) or a comparable volume of commercially-available tissue adhesive (Coseal, n=4 for each endpoint) were placed in the subcutaneous pocket created above the incision. The incision was closed using interrupted sutures (4-0 Vicryl, Ethicon) and 3-6 ml of saline were injected subcutaneously. Up to four implants were placed per animal ensuring no overlap between each subcutaneous pocket created. After 1 day, 3 days, 1 week, or 2 weeks following the implantation, the animals were euthanized by CO2 inhalation. Subcutaneous regions of interest were excised and fixed in 10% formalin for 24 h for histological and immunofluorescence analyses.

Instant Hemostatic Tissue Sealing.

Figures 23A, 23B, 23C, 23D:
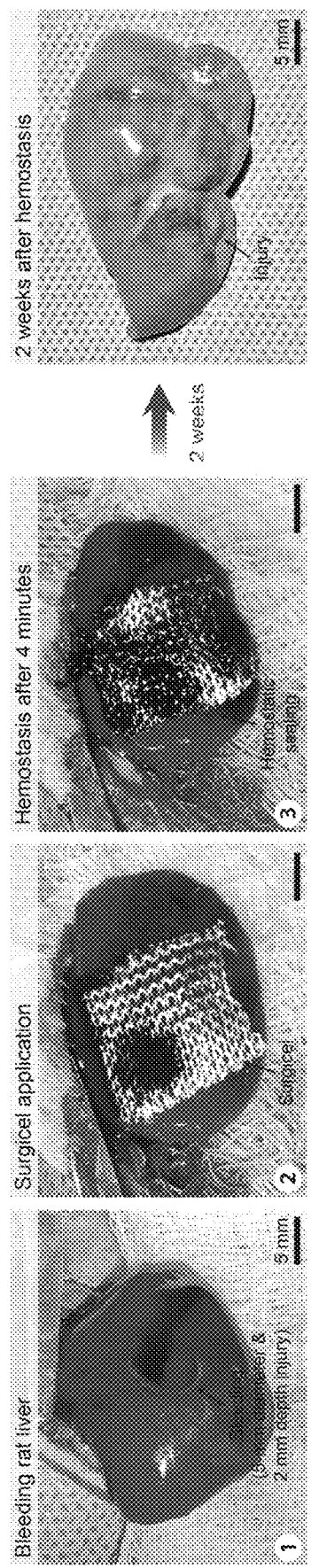
FIGS. 23A-D illustrate the hemostatic sealing of a liver by commercially-available products, where

The present invention tissue adhesive's unique capability of forming instant robust adhesion on blood-covered tissues can be advantageous for rapid and coagulation-independent hemostatic sealing of various tissues in clinical and biomedical applications. To quantitatively evaluate the hemostatic sealing capability of the tissue glue in vivo, the time to hemostasis and blood loss until hemostasis was measured based on rat hepatic and cardiac hemostasis models (FIGS. 21 and 22). The tissue adhesive was shown to achieve hemostatic sealing of bleeding liver (5-mm diameter and 2-mm depth injury) and heart (2-mm diameter ventricular wall injury) within 5 seconds (FIGS. 21A and 22A), giving significantly less time to hemostasis (FIGS. 21C and 22C) and blood loss until hemostasis (FIGS. 21D and 22D) compared to the injury group (without hemostasis) and commercially-available hemostatic agents Surgicel and Coseal (FIGS. 23 and 24). Notably, the injury, Surgicel, and Coseal groups are not able to form hemostatic sealing of heart due to the high pressure and high volume bleeding from a ventricular injury (FIGS. 22C-D and 24), whereas the present invention tissue adhesive forms instant hemostatic sealing of a ventricular injury within 5 seconds, restoring the normal intraventricular blood pressure immediately after hemostasis (FIG. 22E).

Figures 25A, 25B, 25C, 25D:
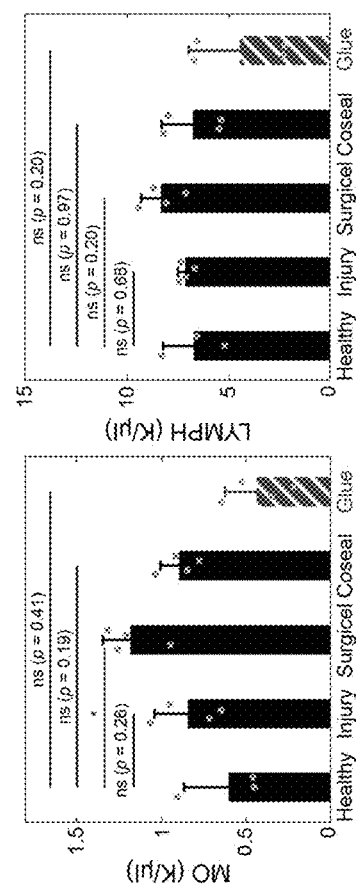
Figures 25E, 25F, 25G, 25H:
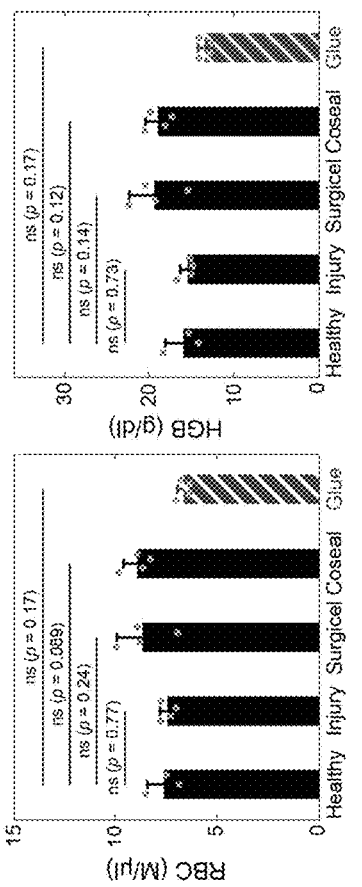

The present invention tissue adhesive was demonstrated to maintain a seal on an injured liver and heart 2 weeks after the initial hemostatic application (FIGS. 21B and 22B). Furthermore, histological analysis of the sealed liver and heart tissues indicated that the tissue adhesive allowed cell infiltration into the crosslinked bioadhesive microparticles and healing of the underlying injuries (FIGS. 21E and 22F-G) Immunofluorescence analysis of inflammatory and foreign body response markers (CD3 20 for T-cell; CD68 for macrophage) show that the present invention tissue adhesive induces the expression of CD3 and CD68 comparable to that of Coseal and significantly lower than that of Surgicel (FIG. 22F-I). Furthermore, complete blood count (CBC) and blood chemistry analysis of the animals 2 weeks after hemostatic sealing demonstrated that the tissue adhesive did not show significant difference in inflammation-related blood cells and markers for organ-specific diseases compared to the healthy animals (FIGS. 25 and 26).

In vivo hemostatic sealing of liver. For hemostatic sealing of the hepatic injury, the animals were anaesthetized using isoflurane (1-3% isoflurane in oxygen) in an anesthetizing chamber. Abdominal hair was removed and the animals were placed over a heating pad for the duration of the surgery. The liver was exposed via a laparotomy. A 5-mm diameter and 2-mm depth injury was made to the heart by using a biopsy punch (Dynarex). To form hemostatic sealing, 0.5 ml of the tissue glue was injected onto the bleeding site and then gently pressed onto the punctured hole using a surgical spatula for 5 sec (n=4). For commercially-available products, Surgicel (Ethicon) with size of 20 mm in length and 20 mm in width (n=4) or 2 ml of Coseal (Baxter) (n=4) were used. For the injury group, no hemostasis was performed (n=4). The amount of blood loss until hemostasis and the time to hemostasis were recorded for each group. After the hemostatic sealing was confirmed, the incision was closed using interrupted sutures (4-0 Vicryl, Ethicon) and 3-6 ml of saline were injected subcutaneously. After 2 weeks following the implantation, blood was collected for blood analysis and the animals were euthanized by $CO_2$ inhalation. Livers with the implants were excised and fixed in 10% formalin for 24 h for histological and immunofluorescence analyses.

In vivo hemostatic sealing of heart. For hemostatic sealing of the full thickness ventricular injury, the animals were anaesthetized using isoflurane (1-3% isoflurane in oxygen) in an anesthetizing chamber. Chest hair was removed. Endotracheal intubation was performed, and the animals were connected to a mechanical ventilator (Model 683, Harvard Apparatus) and placed over a heating pad for the duration of the surgery. The heart was exposed via a thoracotomy and the pericardium was removed using fine forceps. For measurement of intraventricular blood pressure, a pressure-20 volume (PV) catheter (SPR-838, Millar) was inserted into the left ventricle (LV) via apical stick to monitor LV blood pressure during the test. A 2-mm diameter injury was made to the left or right ventricular wall of the heart by using a biopsy punch (Dynarex). To form hemostatic sealing, 0.25 ml of the present invention tissue adhesive was injected onto the bleeding site and then gently pressed onto the punctured hole using a surgical spatula for 5 sec (n=5). For commercially-available products, Surgicel 25 (Ethicon) with size of 20 mm in length and 20 mm in width (n=4) or 2 ml of Coseal (Baxter) (n=4) were used. For the injury group, no hemostasis was performed (n=4). The amount of blood loss until hemostasis and the time to hemostasis were recorded up to 300 sec for each group. After the hemostatic sealing was confirmed, the incision was closed using interrupted sutures (4-0 Vicryl, Ethicon) and 3-6 ml of saline was injected subcutaneously. For groups that failed to form hemostasis until 300 sec, the animals were euthanized by exsanguination. After 2 weeks following the implantation, blood was collected for the blood analysis and the animals were euthanized by $CO_2$ inhalation. Hearts with the implants were excised and fixed in 10% formalin for 24 h for histological and immunofluorescence analyses.

Immunofluorescence analysis. The expression of targeted proteins (αSMA, Collagen I, CD68, CD3) were analyzed after the immunofluorescence staining of the collected tissues. Before the immunofluorescence analysis, the paraffin-imbedded fixed tissues were sliced and prepared into slides. The slides were deparaffinized and rehydrated to deionized water. Antigen retrieval was performed using steam method during which the slides were steamed in IHC-Tek Epitope Retrieval Solution (IW-1100) for 35 min and then cooled for 20 min. Then the slides were washed in three changes of PBS for 5 min per each cycle. After washing, the slides were incubated in primary antibodies (1:200 mouse anti-αSMA for fibroblast (ab7817, Abcam); 1:200 mouse anti-CD68 for macrophages (ab201340, Abcam); 1:100 rabbit anti-CD3 for T-cells (ab5690, Abcam); 1:200 rabbit anti-collagen-I for collagen (ab21286, Abcam)) diluted with IHC-Tek Antibody Diluent for 1 h at room temperature. The slides were then washed three times in PBS and incubated with Alexa Fluor 488 labeled anti-rabbit or anti-mouse secondary antibody (1:200, Jackson Immunoresearch) for 30 min. The slides were washed in PBS and then counterstained with propidium iodide solution for 20 min. A laser confocal microscope (SP 8, Leica) was used for image acquisition. ImageJ (version 2.1.0) was used to quantify the fluorescence intensity of expressed antibodies. All the images were transformed to the 8-bit binary images, and the fluorescence intensity was calculated with normalized analysis. All analyses were blinded with respect to the experimental conditions.

What is claimed is:
1. A method of adhering one or more tissue surfaces covered in one or more fluids comprising:
   (a) applying an adhesive material directly to one or more of the fluid covered tissue surfaces, the adhesive material comprising: a hydrophobic matrix; and a plurality of bioadhesive microparticles dispersed within the hydrophobic matrix, the bioadhesive microparticles comprising: (i) one or more hydrophilic polymers or copolymers; (ii) one or more amine coupling groups, and (iii) one or more cross linkers;
   (b) applying pressure ranging from about 1 kPa to 50 kPa to the adhesive material;
   (c) allowing the hydrophobic matrix to repel and clean the one or more fluids from the tissue surfaces;
   (d) allowing physical bond forming group in the bioadhesive microparticles to form temporary crosslinks by intermolecular bonds; and
   (e) allowing amine coupling groups in the bioadhesive microparticles to form covalent crosslinks with the tissue surfaces.

2. The method of claim 1, wherein pressure is applied for about 5 seconds to about 30 seconds.

3. The method of claim 1, wherein the adhesive material is an injectable adhesive material, and the adhesive material is applied using a syringe.

4. The method of claim 1, wherein the (i) one or more hydrophilic polymers or copolymers are selected from hydrophilic polymers or copolymers that absorb water at a dry state.

5. The method of claim 1, wherein the (i) one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, alginic acid, pectin, and combinations thereof.

6. The method of claim 1, wherein the (ii) one or more amine coupling groups are selected from N-hydroxysuccinimide ester, N-hydroxysulfosuccinimide ester, aldehyde, imidoester, epoxide, isocyanate, catechol, and combinations thereof.

7. The method of claim 1, wherein the (iii) one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof.

8. The method of claim 1, wherein the hydrophobic matrix is selected from silicone oils, mineral oils, essential oils, perfluoropolyether oils, lanolin oils, and combinations thereof.

9. The method of claim 1, wherein the adhesive comprises plurality of bioadhesive microparticles fabricated of (i) poly(acrylic acid) grafted with (ii) N-hydroxysuccinimide ester (PAAc-co-NHS ester) (iii) crosslinked with biodegradable gelatin methacrylate and (i) biodegradable chitosan, dispersed in a silicone oil hydrophobic matrix.

10. The method of claim 1, wherein the adhesive material adheres with an interfacial toughness of at least about 100 J m$^{-2}$, shear strength of at least about 30 kPa and tensile of at least about 10 kPa.

11. The method of claim 1, wherein the physical bond forming groups in the bioadhesive microparticles are carboxylic acid groups which form the temporary crosslinks by intermolecular bonds.

12. The method of claim 1, wherein the bioadhesive microparticles have a particle size ranging from about 10 μm to about 200 μm.

13. The method of claim 1, wherein the adhesive material comprises a ratio between the bioadhesive microparticles and the hydrophobic matrix ranging from about 1:3 to about 1:0.5.

14. The method of claim 1, wherein the one or more fluids are physiological body fluids selected from blood plasma, interstitial fluid, lymphatic fluid, cerebrospinal fluid, gastrointestinal fluid, and combinations thereof.

15. The method of claim 1, wherein after (a) applying an adhesive material directly to one or more of the fluid covered tissue surfaces and prior to (b) applying pressure, the method further comprises applying a backing material to the adhesive material and wherein (b) applying pressure comprises applying pressure to the adhesive material via the backing material.

16. The method of claim 15, wherein the backing material is fabricated of a biocompatible material that does not adhere to wet surfaces.

17. The method of claim 16, wherein the backing material is fabricated of oxidized cellulose, silicone elastomer, polyurethane, hydrogel, any other biocompatible materials that do not adhere to wet tissue, and combinations thereof.

18. The method of claim 1, wherein the one or more tissue surfaces comprise a tissue injury, the method further comprising (f) allowing cell infiltration into the crosslinked bioadhesive microparticles and healing of the underlying tissue injury.

19. A method of healing a tissue injury comprising:
(a) applying an adhesive material directly to the tissue injury, wherein the tissue injury comprises one or more fluid covered tissue surfaces, the adhesive material comprising: a hydrophobic matrix; and a plurality of bioadhesive microparticles dispersed within the hydrophobic matrix, the bioadhesive microparticles comprising: (i) one or more hydrophilic polymers or copolymers; (ii) one or more amine coupling groups, and (iii) one or more cross linkers;
(b) applying pressure ranging from about 1 kPa to 50 kPa to the adhesive material;
(c) allowing the hydrophobic matrix to repel and clean the one or more fluids from the tissue surfaces;
(d) allowing physical bond forming group in the bioadhesive microparticles to form temporary crosslinks by intermolecular bonds;
(e) allowing amine coupling groups in the bioadhesive microparticles to form covalent crosslinks with the tissue surfaces; and
(f) allowing cell infiltration into the crosslinked bioadhesive microparticles and healing of the underlying tissue injury.

20. The method of claim 19, wherein the adhesive material is biodegradable, and wherein the cells replace the biodegrading bioadhesive microparticles to heal the underlying tissue injury.

* * * * *